(12) United States Patent
Scola et al.

(10) Patent No.: US 6,175,644 B1
(45) Date of Patent: Jan. 16, 2001

(54) MACHINE VISION SYSTEM FOR OBJECT FEATURE ANALYSIS AND VALIDATION BASED ON MULTIPLE OBJECT IMAGES

(75) Inventors: Joseph R. Scola, Medfield; Vladimir N. Ruzhitsky, Brookline; Lowell D. Jacobson, Grafton, all of MA (US)

(73) Assignee: Cognex Corporation, Natick, MA (US)

( * ) Notice: Under 35 U.S.C. 154(b), the term of this patent shall be extended for 0 days.

(21) Appl. No.: 09/071,722

(22) Filed: May 1, 1998

(51) Int. Cl.$^7$ ............................................. G06K 9/00
(52) U.S. Cl. ......................... 382/141; 382/190; 382/216; 117/201
(58) Field of Search ................................. 382/107, 141, 382/143, 293, 190, 199, 266, 216; 348/154, 155; 117/14, 15, 201, 202

(56) References Cited

U.S. PATENT DOCUMENTS

| | | | |
|---|---|---|---|
| 3,740,563 | 6/1973 | Reichard | 250/222 |
| 4,277,441 | 7/1981 | Sachs | 422/105 |
| 4,519,041 | 5/1985 | Fant et al. | 364/552 |
| 4,587,617 | 5/1986 | Barker et al. | 364/507 |
| 4,618,989 | 10/1986 | Tsukune et al. | 382/25 |
| 4,760,604 | 7/1988 | Cooper et al. | 382/15 |
| 4,832,496 | 5/1989 | Thomas | 356/384 |
| 5,179,419 | 1/1993 | Palmquist et al. | 356/73.1 |
| 5,189,711 | 2/1993 | Weiss et al. | 382/25 |

OTHER PUBLICATIONS

Cognex Corp., "High–Performance Machine Vision for the VMEbus", pp. 1–8, no date.

Chiou et al., "A Neural Network–Based Stochastic Active Contour Model (NNS–SNAKE) for Contour Finding of Distinct Features," IEEE Trans. On Image Processing, vol. 4, No. 10, Oct. 1995, pp. 1407–1416.

Jacobson, "Conjoint Image Representation and its Application to Viewpoint Invariant Form Recognition and Optical Flow Estimation," Thesis, University of Minnesota, Feb., 1987, pp. 75–76.

Isys, a Cognex Company, iLearn Classifier, Technical Product Bulletin.

Press et al., Numerical Recipes in C, The Art of Scientific Computing, Cambridge University Press, 1988, pp. 290–324.

\* cited by examiner

*Primary Examiner*—Bhavesh Mehta
(74) *Attorney, Agent, or Firm*—Theresa A. Lober

(57) ABSTRACT

Provided is the ability to validate detected features in acquired images to thereby enhance the integrity of any analysis carried out on the detected and validated features. A sequence of images of, e.g., an object is acquired, each image in the sequence corresponding to a distinct orientation of the object about a selected object axis. Images in the sequence are inspected for feature points of the selected feature plane, as-projected into the images, at a first feature detection location and at a second feature detection location. The second feature detection location is configured at an image position at which a feature point detected in the first feature detection location in a first inspected image is expected to appear in a second inspected image. Valid object feature points are identified as being those feature points which are detected in both the first feature detection location in a first inspected image and in the second feature detection location in a second inspected image of the image sequence. Features that are validated are not likely to be time-dependent noise and are preserved for further feature analysis, while extraneous data is rendered transparent to feature analysis. Further, an object feature plane can be analyzed for a specified feature configuration even when only a subset of feature points is available in any one given image of the object, e.g., where a portion of a three-dimensional object obscures other portions of the object in a selected view of the object. Also provided is a method for detecting features of a semiconductor melt surface as a semiconductor ingot is pulled out of the melt.

9 Claims, 17 Drawing Sheets

U.S. PATENT DOCUMENTS

| | | | |
|---|---|---|---|
| 5,331,413 | 7/1994 | Diner | 348/114 |
| 5,426,684 | 6/1995 | Gaborski et al. | 378/62 |
| 5,437,242 | 8/1995 | Hofstetter et al. | 117/14 |
| 5,625,702 * | 4/1997 | Kamada et al. | 382/107 |
| 5,653,799 | 8/1997 | Fuerhoff | 117/14 |
| 5,656,078 | 8/1997 | Fuerhoff | 117/201 |
| 5,730,026 | 3/1998 | Maatuk | 73/295 |
| 5,734,742 * | 3/1998 | Asaeda et al. | 382/141 |
| 5,734,751 | 3/1998 | Saito | 382/203 |
| 5,882,402 | 3/1999 | Fuerhoff | 117/201 |
| 5,892,538 | 4/1999 | Gibas | 348/43 |

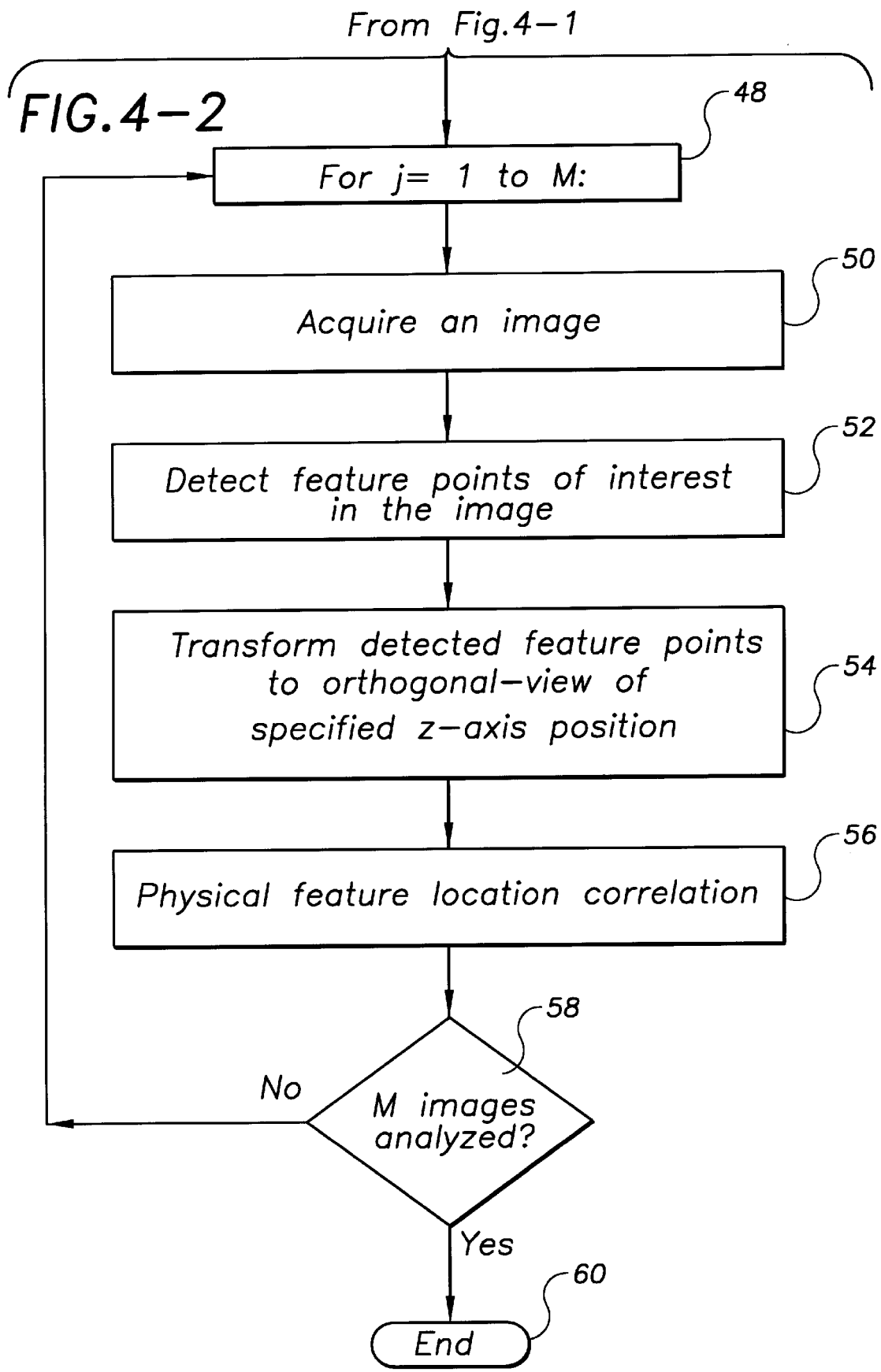

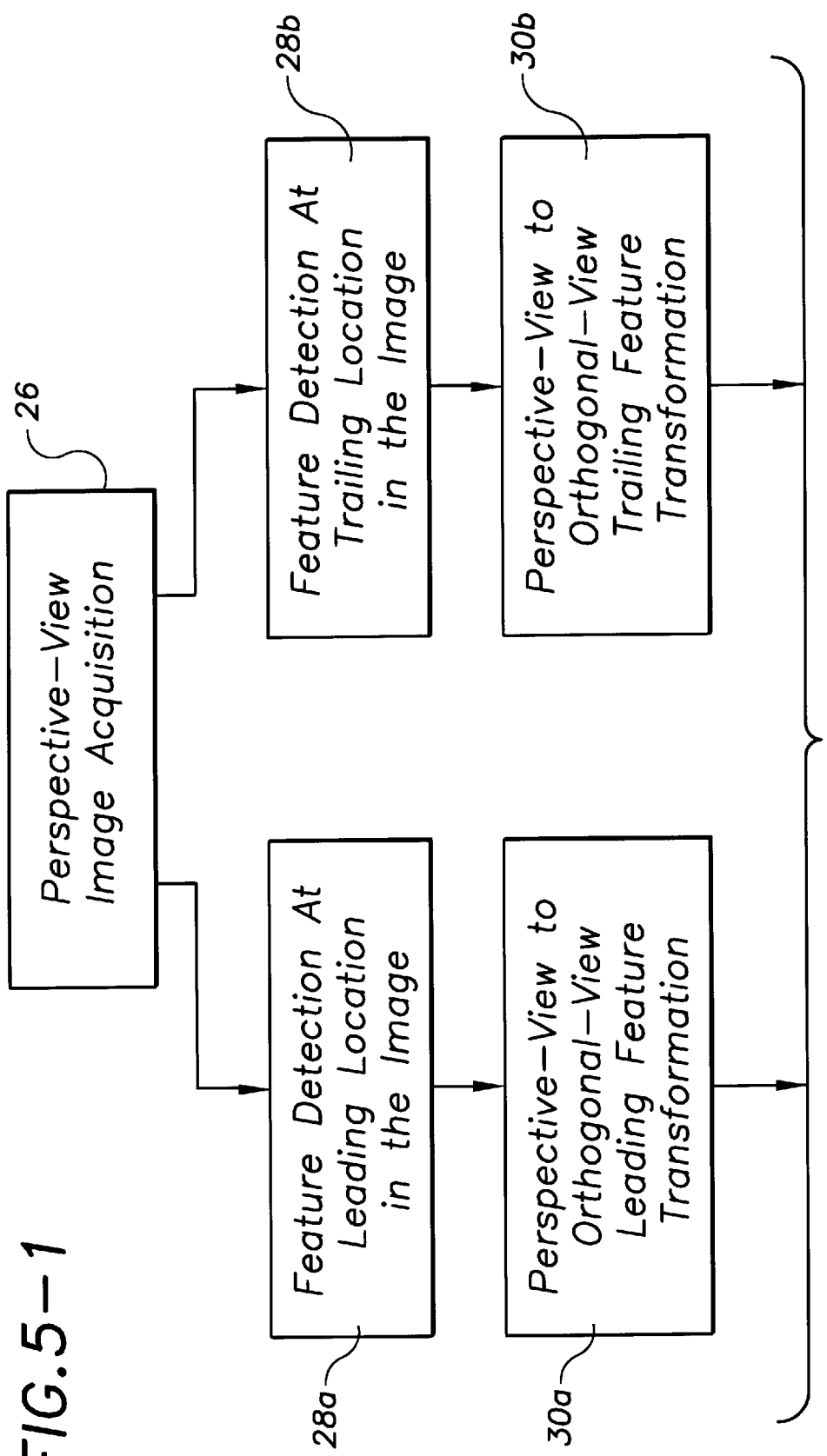

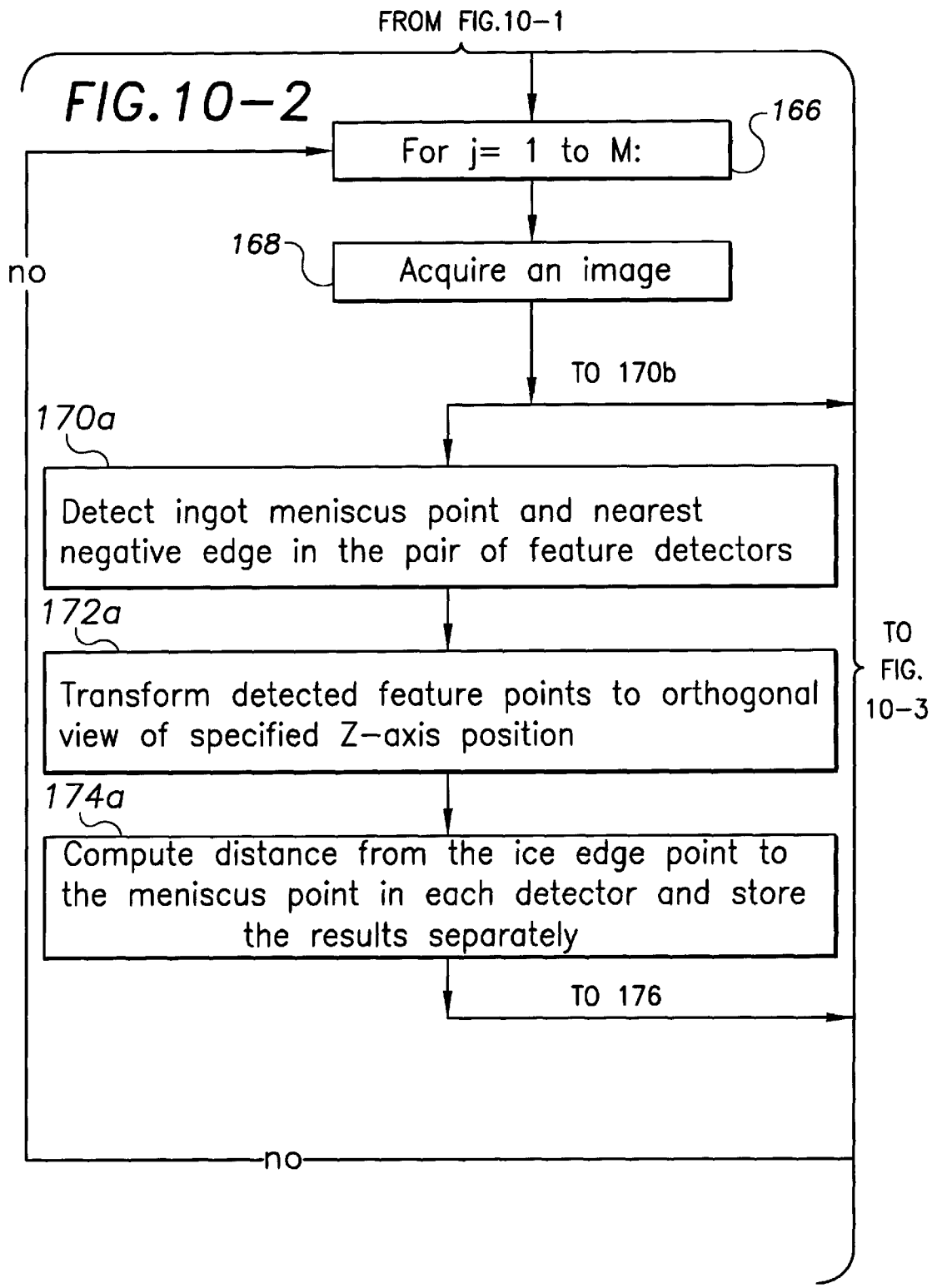

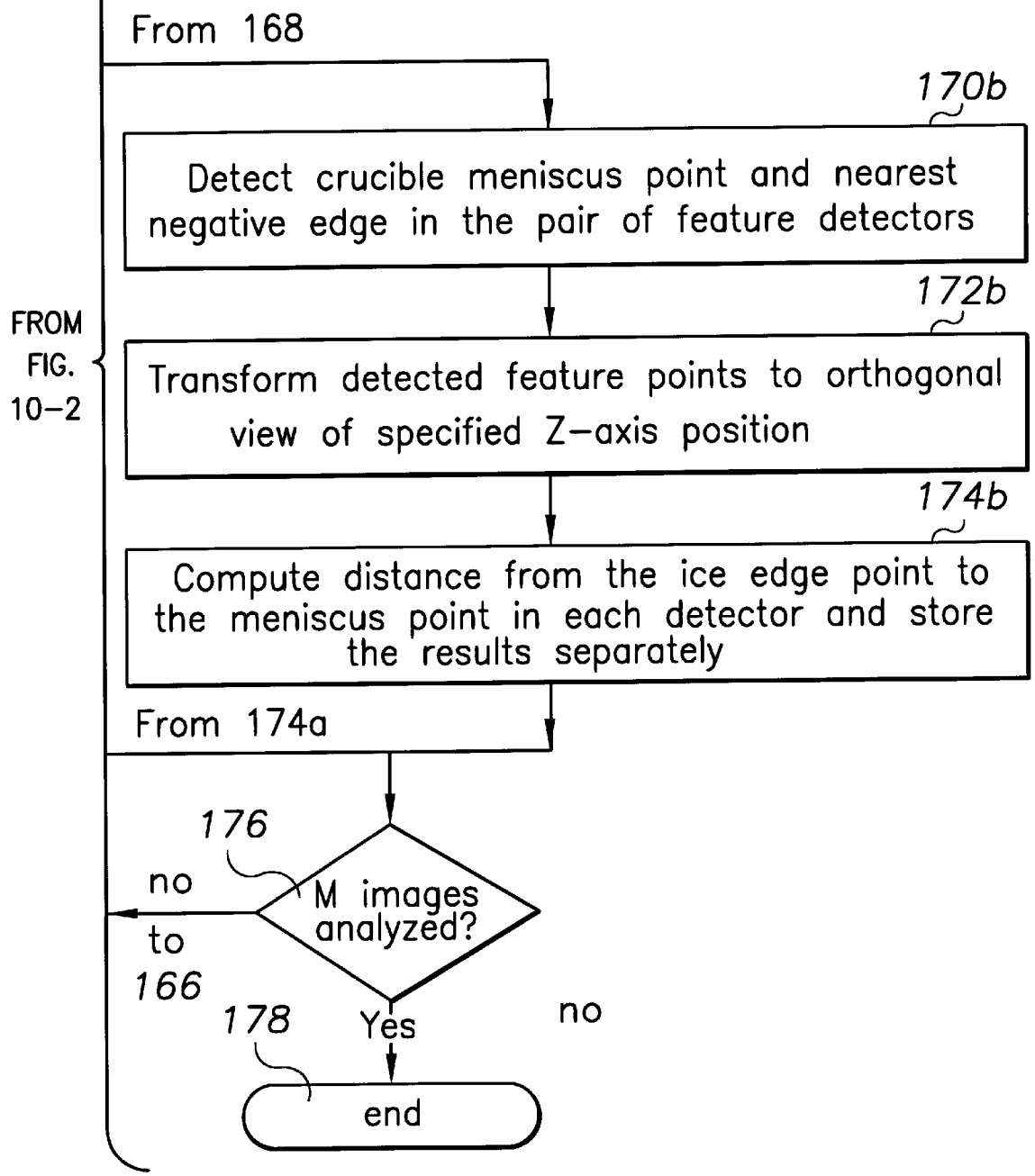

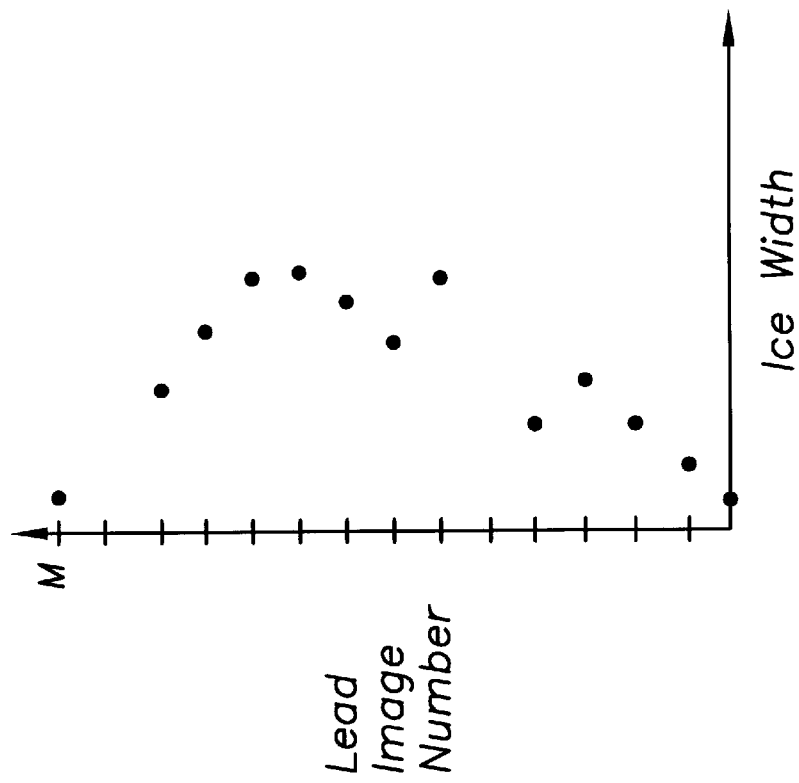

MACHINE VISION SYSTEM FOR OBJECT FEATURE ANALYSIS AND VALIDATION BASED ON MULTIPLE OBJECT IMAGES

FIELD OF THE INVENTION

This invention relates to machine vision for industrial processes, and more particularly relates to machine vision techniques for analyzing feature information about an object based on an acquired image of the object.

BACKGROUND OF THE INVENTION

Machine vision systems are increasingly employed to replace human vision in a wide range of industrial processes such as manufacturing operations. A machine vision system typically provides automated, computer-based image acquisition and analysis capabilities that can be employed for tasks such as, e.g., measurement and inspection of parts or materials, or monitor of the state of a manufacturing process. For such tasks, a machine vision system typically is configured with a camera for acquiring an image of a process environment or an object of interest, e.g., a part being produced, and further is configured with processing functionality to process the acquired image and produce information about the process or object. Frequently, in part measurement or process monitoring tasks, the object image acquisition and analysis functions are tailored to extract and analyze specific process and/or object features that are of interest for the selected task and given manufacturing process.

For many manufacturing environments, reliable machine vision analysis of images of the manufacturing process is made difficult by variable and sometimes unpredictable conditions in the environment. For example, changes in the surface characteristics of a part under analysis can cause unexpected fluctuations in part features as they appear in images of the part, leading to potentially faulty conclusions being made about the part based on the images. Similarly, changes in lighting conditions of a manufacturing process or in the reflectivity of parts involved in the process can cause shifts in features as they appear in images of the process, leading to potentially faulty conclusions being made about the process status based on the images. Optical and/or electrical noise generated by the manufacturing process systems can further exacerbate fluctuations in imaged features of a part or process and in addition can introduce spurious, invalid feature data.

But optimally, machine vision analysis of a manufacturing process or part being processed is based on imaged features of interest for which there is associated a high degree of confidence in their validity. Inconclusive and unreliable analyses can otherwise result. This is especially true for complicated manufacturing processes characterized by a high degree of unpredictability in conditions of the process which are to be analyzed. Ideally then, machine vision image analysis and feature extraction is robust with respect to variability, noise, unpredictability, and other such characteristics of a process to be monitored.

Conventional machine vision filtering and thresholding techniques, while typically capable of compensating for predictable, generally uncomplicated image feature fluctuation and noise, cannot typically accommodate unpredictable and complex image feature shifts and noise introduction. In addition, typical filtering operations can affect "useful," i.e., meaningful, data as well as extraneous, stray noise data. If the extraneous noise data is substantial, its removal can distort features of interest to an extent at which they lose meaning. As a result, noise removal operations preferably must be combined with complicated feature analysis operations to maintain integrity of the data.

Machine vision image acquisition and analysis is further complicated for a range many manufacturing processes in which full-view image acquisition of a part or process environment cannot be accomplished. Specifically, for complicated three-dimensional object shapes, and more specifically for complicated opaque objects, and for manufacturing tooling configurations, one or more process or object regions may obscure other such regions from the line-of-sight view of an image acquisition camera's position. As a consequence, it may not be possible from a single camera position to simultaneously view related processes or object features such as circumferential points of a complete cross-sectional object profile. In other words, unlike that of substantially two-dimensional objects or a two-dimensional object face, related features of a complicated and opaque three-dimensional object or process environment are not guaranteed to be together fully exposed for simultaneous image acquisition. Instead, only a portion of the object and a subset of related object features are likely to be fully exposed to a single image acquisition camera angle.

The complications of this scenario are compounded in many applications where the location of a single image acquisition camera is limited by the manufacturing environment; e.g., where an optimum camera location cannot be accommodated. For example, in a scenario where an orthogonal, top-down view of a three-dimensional object may be known to encompass a complete set of object features, such vertical location of the camera may not be practical. For a large class of manufacturing applications, accommodation can be made for only a single, oblique camera location that results in a acquisition of only a perspective view of an object; and for some camera angles this can result in a large fraction of related object features being obscured in the object image.

A further complication is added for machine vision applications in which an object to be viewed is moving, e.g., rotating, during the process being monitored. In this case, a different subset of related features, e.g., a different portion of an object's cross-sectional profile or shape, is in view of the camera's line-of-sight at any given time. Traditional vision system techniques, developed typically for orthogonal image acquisition and analysis of substantially two-dimensional object surfaces, are generally ineffective at addressing these combinations of complicated object configurations, object movement, and manufacturing constraints. The unpredictability, variability, and noise conditions often characteristic of such scenarios further are not effectively addressed by traditional vision system techniques, resulting in potentially questionable validity of machine vision image analysis of such scenarios.

SUMMARY OF THE INVENTION

The invention provides the ability to validate detected features in acquired images to thereby enhance the integrity of any analysis carried out on the detected and validated features. In a machine vision method provided by the invention for detecting features of an object in a selected feature plane of the object, a sequence of images of the object is acquired, each image in the sequence corresponding to a distinct orientation of the object about a selected object axis. Images in the image sequence are inspected for feature points of the selected feature plane, as-projected into the images, in a first feature detection location. Images in the image sequence are also inspected for feature points of the selected feature plane, as-projected into the images, in a second feature detection location. The second feature detection location is configured at an image position at which a feature point detected in the first feature detection location in a first inspected image is expected to appear in a second inspected image. Valid object feature points are identified as being those feature points which are detected in both the first feature detection location in a first inspected image and in the second feature detection location in a second inspected image of the image sequence.

The invention provides a wide range of adaptations of this technique; for example, images in the image sequence can be inspected for feature points of the selected feature plane, as projected into the images, in a number, n, of feature detection locations. Here the n feature detection locations are configured with respect to each other at image positions based on an expected shift in image location of a given feature point between two consecutive images in the image sequence. Then valid object feature points are identified as being those feature points which are detected in a specified minimum number of the n feature detection locations each in a different image of the image sequence.

With the techniques provided by the invention, the authenticity of object features can be validated without the need for prespecified knowledge of expected changes in the object or in the process environment. Spurious, time-dependent noise or object characteristics typically will appear in only one of the feature detection locations, and are automatically disregarded by the validation process. Features that are validated are not likely to be time-dependent noise and are preserved for further feature analysis, while extraneous data is rendered transparent to feature analysis.

Complicated and unpredictable three-dimensional object and feature sizes and shapes are accommodated by the techniques as surface feature information is extracted and analyzed. Specifically, a selected object feature plane can be analyzed for a specified feature configuration even when only a subset of feature points is available in any one given image of the object. Such can be the case, e.g., where a portion of a complicated three-dimensional object obscure other portions of the object in a selected view of the object. A wide range of machine vision applications for inspection, monitoring, and measurement of object features, object configurations, and process environments, and other such scenarios, are thereby enabled by the invention.

Given inspection of images at two feature detection locations, in embodiments provided by the invention valid object feature points are identified as being those feature points which are detected in both the first feature detection location in a first inspected image and in the second feature detection location in a second inspected image of the image sequence, as explained above. Here the second inspected image can be later in the image sequence than the first inspected image. The first and second inspected images can be consecutive images in the image sequence, or can be separated in the image sequence by a number, e.g., two, of intermediate images in the sequence.

In embodiments provided by the invention, the second feature detection location can be configured at an image position that is based on a distance through which a feature point that is detected at the first feature detection location, in the first inspected image, is expected to shift between the first and second inspected images. The expected feature point shift can be a rotation, translation, or progression. Identification of valid object feature points can be carried out by logical ANDing of a detected feature point image corresponding to the first inspected image and a detected feature point image corresponding to the second inspected image.

In other embodiments provided by the invention, the acquired object images can be of a selected view of the object, and detected object feature points can be associated with an orthogonal view of the selected feature plane. For example, the acquired object images can be perspective-view images. In this case, feature points are identified as-projected into the perspective-view images. Feature points can here be associated with an orthogonal feature plane view by mapping feature points from a two-dimensional image coordinate system that is parallel with the selected perspective view to a three-dimensional coordinate system that is aligned with the selected object axis. The resulting orthogonal feature plane view can then be analyzed for a specified feature configuration. For example, feature points can be correlated with corresponding physical orientations of the selected feature plane, based on order position of images in the sequence and by angular object orientation offset between adjacent images in the sequence.

Prior to identifying valid object feature points, representations of the detected feature points can be adjusted to compensate for detection location inaccuracy.

In general, object images can be acquired as a sequence of images, e.g., a video sequence. A portion of each image in the sequence preferably is in common with a portion of a consecutive image in the sequence. If the object is rotating about the selected axis, then to capture images of all sides of the object, the number of images in the sequence is preferably at least a minimum number, M, of images, where M is selected as $M=T_0/T_a$, where $T_0$ is a period of revolution of the object and $T_a$ is a period required for acquiring one image.

The sequence of images can be taken from a fixed viewing location as the object rotates about the selected object axis or alternatively, an image acquisition camera can be rotated about the selected object axis, e.g., while the object remains stationary. The selected object axis can be perpendicular to the selected object feature plane, e.g., with the selected object axis operating as a vertical axis of revolution and the selected feature plane being a horizontal plane located at a position along the axis of revolution. The feature points to be identified in the feature plane can be circumferential feature points of the object.

To carry out in inspection of images at feature detection locations, an edge detection region can be applied at each of the n feature detection locations. Each edge detection region is searched for an edge of a feature point, and positions of the detected edges are correlated to feature point positions.

The invention provides, in a related aspect, a machine vision method for detecting features of a semiconductor melt surface from which a semiconductor crystal ingot is pulled as the ingot and melt are rotated about a vertical axis of rotation. Here a sequence of perspective-view images of the melt surface is acquired from a fixed viewing location, with each image in the sequence corresponding to a perspective view of a distinct orientation of the melt about the vertical axis of rotation. Images in the image sequence are inspected for melt surface feature points, as projected into the images, at a number, n, of feature detection locations. The feature detection locations are configured with respect to each other at image positions based on an expected shift in image location of a given melt surface feature point between two consecutive images in the image sequence. The detected melt surface feature points are mapped from a perspective-view image projection to an orthogonal-view projection of the melt surface; and valid melt surface feature points are identified as being those feature points which are detected in a specified minimum number of the n feature detection locations each in a different image of the image sequence.

In embodiments provided by the invention, the valid melt surface feature points can be contour points of solid-phase crystal regions on the surface of the melt. Such solid-phase crystal regions can nucleate at the ingot and/or can nucleate at a wall of a crucible in which the melt is contained.

The solid-phase crystal region contour points can be analyzed in accordance with the invention to, e.g., determine an extent of the melt surface that is free of the solid-phase crystal, e.g., the extent of melt surface between solid-phase crystal regions nucleating at the ingot and nucleating at the crucible. The solid-phase crystal region contour points can also be analyzed in accordance with the invention to determine the area of the solid-phase crystal region.

This melt surface analysis enables a robust, real time, automated machine vision monitoring of a crystal ingot growth process to provide process control that is generally more responsive and efficient than human process operator control. The automated control enables the early warning of solid-phase crystal growth, which under certain circumstances can severely damage the growth apparatus and can impact the quality of the crystal ingot itself. Other features and advantages of the invention will be apparent from the claims, and from the following description and accompanying drawings.

BRIEF DESCRIPTION OF THE DRAWINGS

FIG. 13A is a plot of ingot ice contour width for images in an acquired sequence of a number, M, of images, detected by a lead ingot feature detector; and FIG. 13B is a plot of ingot ice contour width for images in an acquired sequence of a number, M, of images, detected by a trailing ingot feature detector.

DETAILED DESCRIPTION OF THE INVENTION

Figure 1:
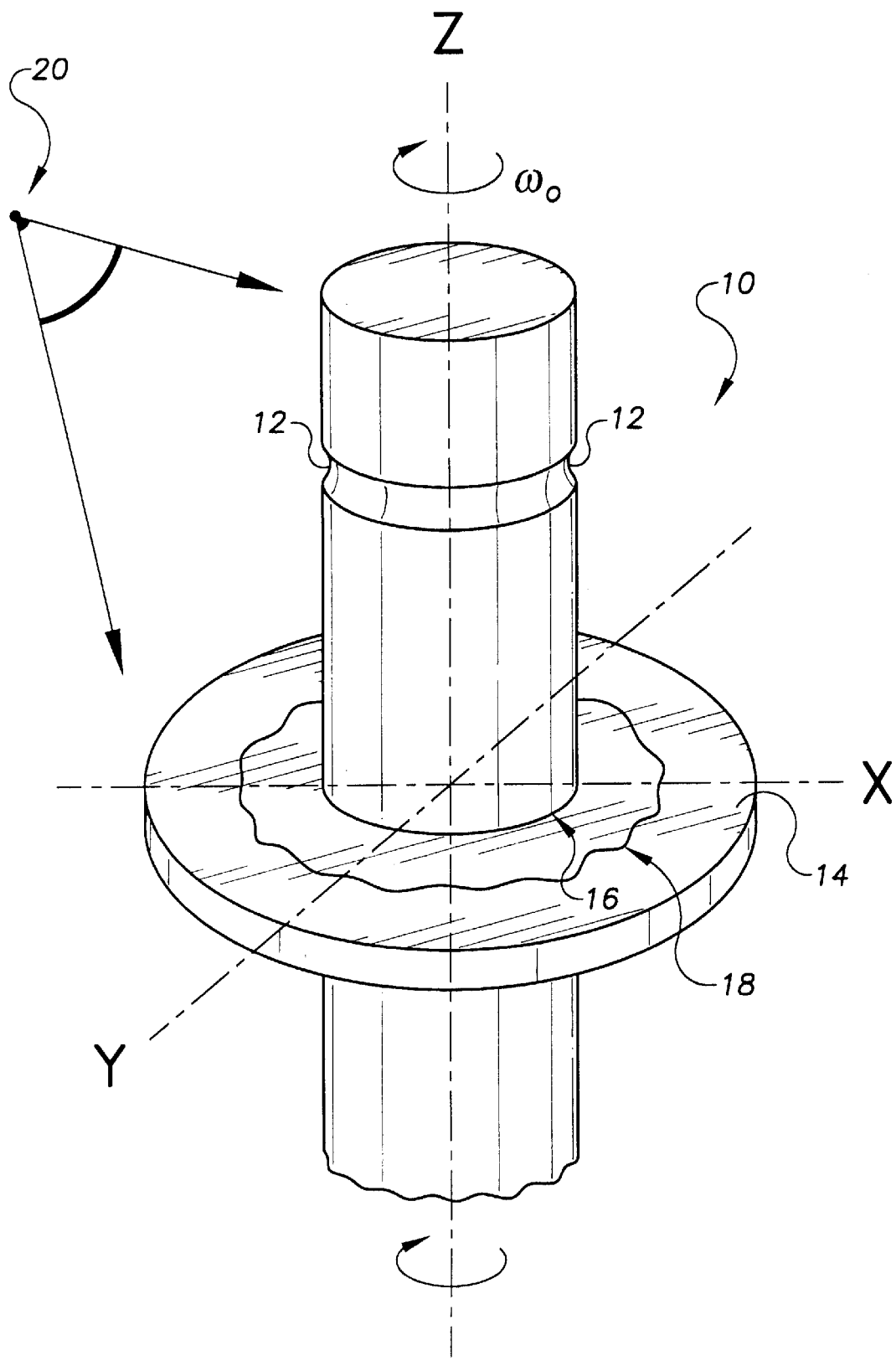
FIG. 1 is a schematic representation of an example object to be analyzed by the machine vision techniques provided by the invention.

FIG. 1 illustrates a generalized and example three-dimensional object 10 for which feature analysis is enabled by the invention. The object is described in an orthogonal physical coordinate system with an X-axis, Y-axis, and Z-axis as shown. The object can include a variety of features, e.g., profile features such as a sidewall notch 12 and the edge of an extended planar section 14; planar features such as a section junction 16 and a face feature 18, as well as other object features. The features shown in the figure are for example only and it is to be understood that a wide range of other object features and related object configurations can be included. For example, the configuration can be representative of a manufacturing process environment in which, e.g., a planar section 14 relates to a feature of a part, tooling arrangement, or feed material employed in the manufacturing process. The object or manufacturing process configuration need not necessarily be circular; other cross-sectional object shapes and process configurations can also be accommodated.

For clarity, the example configuration of FIG. 1 will be considered as an object to be processed, but it is to be recognized that such can also be considered as a process environment. The object rotates about an axis of rotation, shown here as the Z-axis, at a known rotational speed, $\omega_0$. A viewing location 20 is specified as that location from which a perspective-view image of the rotating object is to be acquired. For a given selected viewing location 20, various vertical surfaces of the object can be observed, and one side of planar object surfaces, e.g., the surfaces shown orthogonal to the axis of rotation, can also be observed, with the observable side of a given planar surface defined by the vertical location of the planar surface with respect to the viewing location. The viewing location 20 is thus preferably selected such that the side of a planar surface of interest is observable. The viewing location is not limited to the particular perspective view shown and in general, can instead be a parallel, perpendicular, or other view.

As the object rotates, the acquisition of images of the object, taken from the vantage point of the viewing location, results in a sequence of perspective-view images that each correspond to a portion of the object in view, from the viewing location, at the given time of that image acquisition in the sequence. Accordingly, the merging of images in such an image sequence collected during at least one complete object revolution provides an integral perspective-view representation of the object. This technique is exploited in accordance with the invention to enable the acquisition of a complete perspective view of an object, using only one image acquisition camera, and even as the object rotates.

Figure 2:
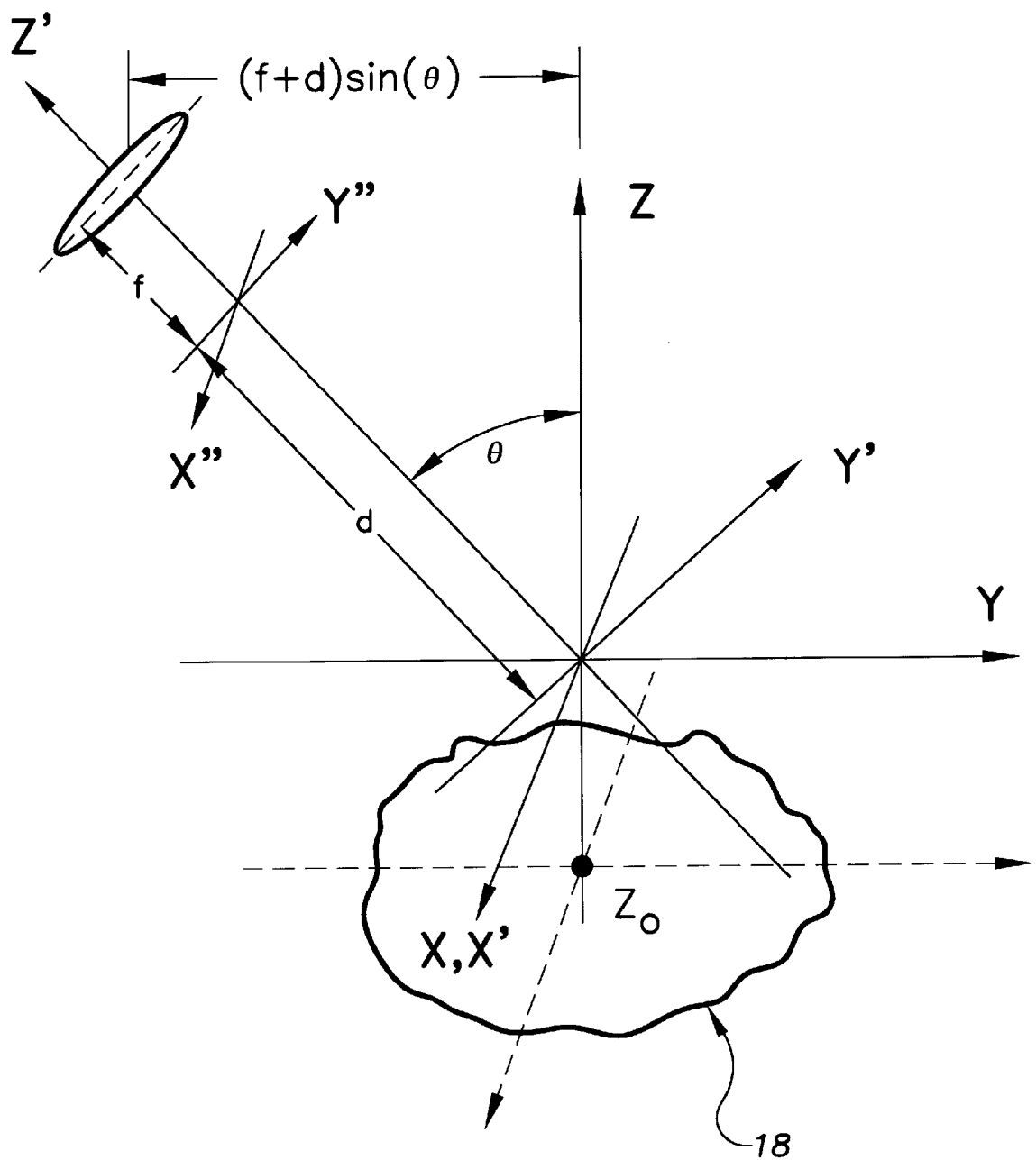
FIG. 2 is a plot of the physical, viewing, and image coordinate systems defined by the object orientation of FIG. 1.

Considering the planar feature 18 shown in the object 10 of FIG. 1, this perspective-view image acquisition process produces an image that contains a perspective-view projection of the planar feature 18 into an image plane; in general, all object features will be projected to a perspective-view by the image acquisition process. The various coordinate systems that define this projection are shown in FIG. 2 with the example planar feature 18. The physical coordinate system of the object, as shown in FIG. 1, is an orthogonal coordinate system having an X-axis, Y-axis, and Z-axis. The viewing location of the image acquisition camera corresponds to a viewing coordinate system that is also an orthogonal system, having an X'-axis, Y'-axis, and Z'-axis. This viewing coordinate system is rotated from the physical coordinate system by a viewing angle, $\theta$, which corresponds to a rotation of the viewing coordinate system about the X-axis of the physical coordinate system. In other words, the X- and X'-axes are aligned, and the Y'- and Z'-axes are rotated by the viewing angle, $\theta$, from the Y- and Z-axes, respectively.

The object image acquired by the camera is two-dimensional in nature and accordingly corresponds to a two-dimensional image coordinate system, having an X"-axis and a Y"-axis. The image coordinate system is aligned with the perspective-view orientation of the viewing location, as shown in FIG. 2, and thus is parallel with X'- and Y'- axes of the viewing coordinate system. The location of the camera at the viewing location is specified as a distance, d, of the camera position from the Z'-axis origin of the viewing coordinate system, and for a given lens configuration the focal length, $f$, of the camera is also specified along the Z'-axis, taken from the camera location. With these metrics, the location of the camera with respect to the physical coordinate system origin is given as a distance $(f+d)\sin(\theta)$ along the Y-axis.

The systems and techniques of the invention provide the ability to analyze object features in the object's physical coordinate system even though the features are captured in a perspective-view image of the object. The systems and techniques provided by the invention further provide the ability to analyze a complete set of related features or feature points even though only a subset of the features or feature points may be available in a given acquired object image in a sequence of acquired object images.

Figure 3:
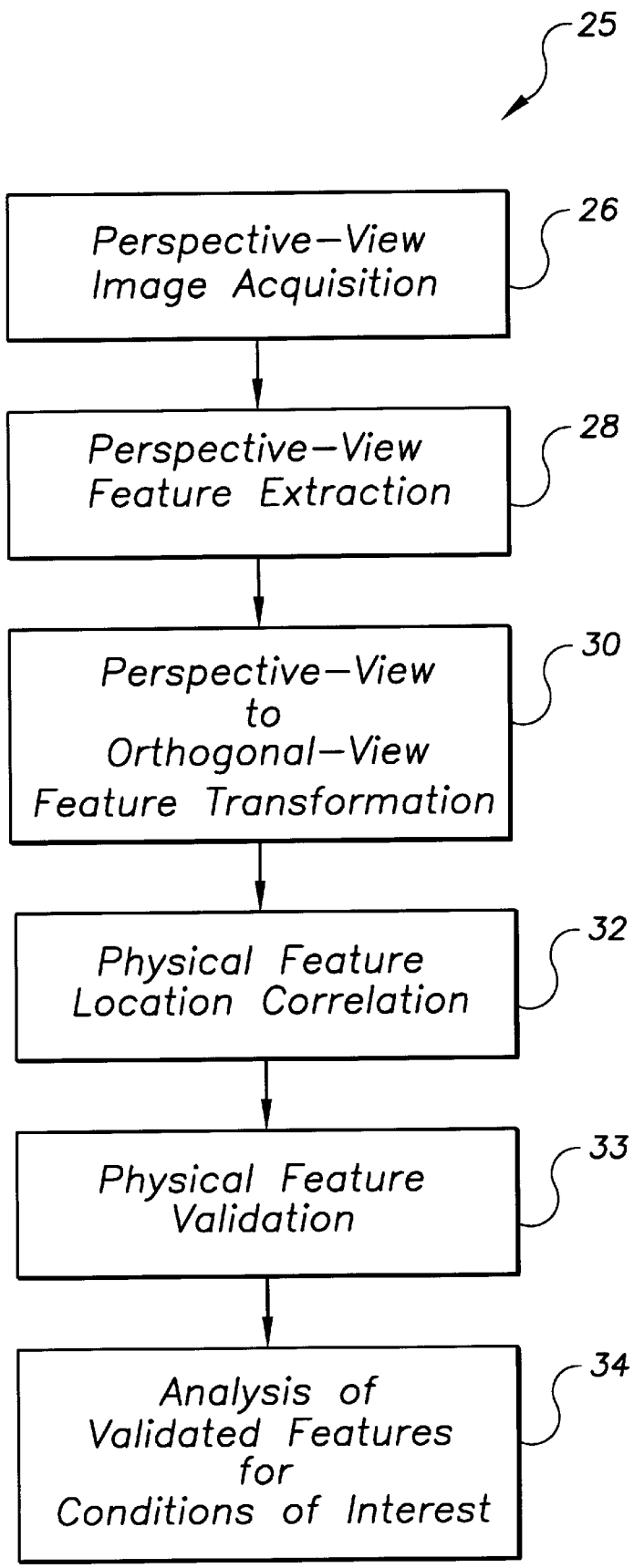
FIG. 3 is a flow diagram of a machine vision technique provided by the invention for acquiring perspective-view images of object features and analyzing the features with reference to an orthogonal view of the physical feature location on the object.

Referring to FIG. 3, these abilities are provided in a machine vision system technique 25 where in a first step 26 a sequence of perspective-view images of an object is produced while the object rotates, e.g. while the object undergoes a manufacturing process. In a next step 28 features of interest are extracted from the perspective-view image. Then a step 30 is carried out to transform the perspective-view images of the extracted features to an orthogonal view feature representation that corresponds to an orthogonal view of the features in the physical coordinate system of the object. The transformed features are then processed in a step 32 that correlates each feature, e.g., with respect to a common, feature-independent physical location, with respect to a corresponding, feature-dependent object location, or based on another such physical correspondence. With this correlation complete, an orthogonal view of a full set of features of interest, mapped to the physical coordinate system of the object, is produced. In a next step 33, the set of features is analyzed to validate as true features only those which meet validation criteria, described below. The resulting validated feature set is then available for further analysis such as a step 34 of feature analysis for a condition or conditions of interest.

Figures 1, 4:
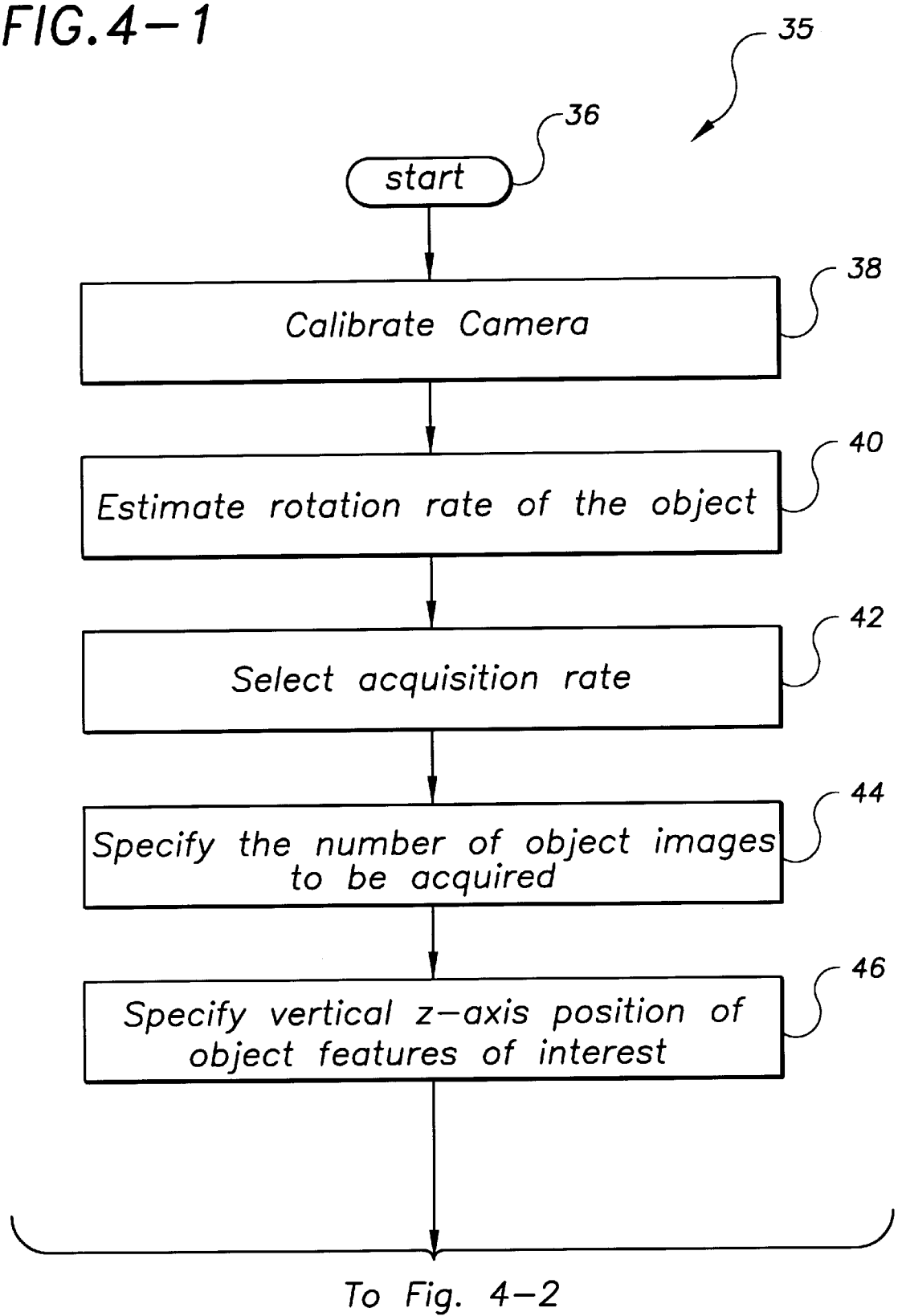
FIG. 4 is a flow diagram of a machine vision technique provided by the invention that is an adaptation of the technique of the FIG. 3 flow diagram, for acquiring perspective-view images of object features on a rotating object and at a selected plane of the object.

FIG. 4 provides a flow diagram of an example of steps 26–30 of this machine vision system technique, here adapted as a technique 35 for enabling the analysis of object features that are known to together reside in a given plane, e.g., a plane that is perpendicular to the Z-axis, of an object or system under consideration. It is common in machine vision applications for an expected location of a feature or set of features of interest to be known, and further for the features to reside together in a common plane of the object or the system under consideration. As can be recognized, the techniques of the invention can be adapted for a given feature plane of interest, and is not limited to a horizontal or vertical feature plane orientation.

At the starting step 36 of the technique, the physical coordinates of an object to be analyzed are defined and a viewing location is selected at which an image acquisition camera is positioned. Then in a calibration step 38 the camera is calibrated based on the orientation of the viewing coordinate system with respect to the object's physical coordinate system. With reference back to FIG. 2, The viewing angle, $\theta$, between the Z'-axis of the viewing coordinate system and the Z-axis of the physical coordinate system is specified, and the camera and focal length distances, d and $f$, respectively, are specified. The camera is then calibrated based on these metrics to set the camera's image reference coordinates. The camera is also calibrated based on the geometry of its image acquisition region. For example, a charge-coupled-device (CCD) camera is characterized by regions of pixels that capture an image; the distance between the centers of two adjacent CCD pixels must be known to enable correlation of pixel size to physical scene size.

In a next step 40 of the technique, the rotation rate, $\omega_0$, of the object under consideration is estimated. This can be accomplished in any of a number of suitable and conventional methods, e.g., using an encoder sensor, or from a priori knowledge of the parameters of the process being carried out on the object. From the object's rotation rate, $\omega_0$, then can be computed the object's period of rotation, $T_0$, where $T_0=1/\omega_0$. This is the time required for the object to make one complete revolution, and is the time required for an observer at the viewing location to have observed an entire perspective view of the object.

In a next step 42 the rate at which object images can be acquired by the image acquisition camera, as the object rotates, is specified. The acquisition period, $T_a$, corresponding to the specified acquisition rate, is a function of the finite amount of time required by the camera to physically produce an image of a scene; e.g., a charge-coupled-device camera requires a finite amount of photon collection time to produce an image. The acquisition period of a given camera is typically a known parameter for the camera.

At this point, a next step 44 can be completed to specify the number, M, of object images to be acquired for producing an integral object perspective view. The number, M, of specified object images corresponds to the number of images that will be available for detecting and analyzing object features of interest. Accordingly and preferably, images are acquired for at least one period of revolution of the object. The number, M, of specified object images to be acquired in an image sequence can be specified as:

$$M = n\frac{T_0}{T_a}; \text{ where } n \geq 1; \tag{1}$$

where n is the number of object revolutions to be included during the image acquisition sequence. When the value of n is 1, the number of acquired images, M, is the minimum number required to include images from one entire period of revolution of the object. Here it is assumed and preferred that the image acquisition process be carried out at a constant rate. It is seen that for a given period of object revolution, a relatively shorter acquisition period enables a larger number of images to be acquired during one revolution of the object. For some applications, depending on the frequency of features to be analyzed, it may accordingly be preferable to adjust the camera operation such that the acquisition time is minimized and the object image sampling frequency is increased.

In a next step 46, the vertical position, i.e., the Z-axis position, of the object plane at which the features of interest are expected or known to be located is specified. As mentioned above, for many applications, the Z-axis location of features to be analyzed is a priori specified by the application process. If the Z-axis feature plane position is not prespecified, it can be estimated using, e.g., analytical machine vision techniques for detecting feature plane position within a general expected window of positions.

A preferred technique for analytically determining a Z-axis feature plane position is described by Lowell D. Jacobson in U.S. Ser. No. 08/758,426, filed Nov. 29, 1996, entitled "Vision System For Estimating a Radius Profile of a Solid-Of-Revolution," assigned to the assignee of the present invention, and the entirety of which is hereby incorporated by reference. Briefly, in this technique, at least one perspective-view image of the object is acquired, and a feature detection process, such as an edge detection process, is then carried out on the image to locate the object features of interest and compare their locations with a hypothetical Z-axis position. The hypothetical Z-axis position value is based on an expected Z-axis position for the features of interest. If the detected features are found to define a feature plane that well-corresponds to the hypothetical Z-axis feature plane position, then numerical methods are employed to estimate the true Z-axis position of the feature plane. If the plane of the located features is found not to correspond to the hypothetical Z-axis position, then the hypothesis is iteratively adjusted until correspondence is made. This technique as described by Jacobson can be generalized to a wide range of object, material, and system features. As can be recognized, alternative techniques for estimating the Z-axis feature plane position can also be employed as-suitable for a given application.

With the Z-axis feature plane position specified, an iterative loop 48 is carried out a number, j=1 to M, times, corresponding to the number, M, of object images specified for acquisition. As explained above, this acquisition of a sequence of M images produces a sequence of M "snapshots" of the rotating object. The image sequence can be interpreted as a series of images produced by a camera as the camera is rotated about a stationary object; after each rotation of the camera by a specified interval angle, an additional "snapshot" is produced for the series. Thus, in a first step 50 of the loop 48, an image of the object is acquired.

In a next step 52 feature points of interest are detected in the just-acquired image. This process can be carried out by, e.g., detection of all feature points in the image and then retention from the detected set of only the one or more feature points of interest i=1 top, where p is the total number of detected and retained feature points. A wide range of feature detection techniques are well-established and can be employed here as found suitable. Feature point detection is given here as a specific example of a more general feature point identification process contemplated by the invention. Identification of feature points is meant to refer to any machine vision process that enables distinguishing of feature points from other surrounding image areas such that an extraction of a feature point representation can be accomplished.

Generally, detected feature points are defined as image locations in the specified Z-axis feature plane that are characterized by an image intensity value that is different, in some specified manner, from the intensity values of surrounding image locations. A feature point can thus consist of an image pixel, a patch of pixels, a line of pixels, or other pixel grouping, and in general is a single pixel or a neighborhood of pixels. Features can be distinguished generally by an intensity difference, i.e., a degree of contrast, or more specifically, a defined edge. Edge detection within the image thereby provides one broadly applicable technique for feature point identification within the image.

In one popular edge detection technique, employing a Sobel operator, raw image intensity data for the entire image is converted to a corresponding edge image which identifies all edges throughout the image. A determination of which edge points in the edge image correspond to the object features of interest can then be made using, e.g., filtering techniques. This is an exhaustive edge detection technique in that it considers all possible edge points in the object image. While the technique provides a high degree of accuracy in feature detection, it requires significant computation time and thus for many applications may not be warranted.

An alternative, less computationally-intensive feature detection technique can instead be employed, preferably like the edge detection technique described by Jacobson in the patent application referenced above and incorporated herein by reference. Here a commercial edge detection tool, e.g., the machine vision system Caliper Tool from Cognex Corporation, of Natick, Mass., is applied to the image in a manner that corresponds with the Z-axis estimate for the feature plane of interest. Alternatively, a Z-axis estimate can be produced as an integral task of the feature detection step. Briefly, using this Caliper Tool, edge detection regions are applied to hypothesized feature locations of the image expected to correspond to edges of the features to be detected. For each edge detection region there is computed the gradient of the image intensity profile along a specified search direction, and then is determined the peak in the resulting gradient profile that satisfies specified feature expectations such as feature edge direction. If the determined peak is found to satisfy a confidence threshold, then it is judged that an edge of a feature of interest has been detected. If edges are not detected for a given orientation of edge tools, then the hypothesized feature locations are iteratively adjusted until feature edges can be detected.

Once the edges of features are detected, one or more features can be retained as being those of interest using, e.g., a conventional comparison technique or other suitable metric depending on the given application. The corresponding positions of the retained feature or features, referenced to the two-dimensional image coordinate system of FIG. 2, are then stored for processing. Specifically, a data structure is produced that indicates for each of the one or more i=1 top retained feature points located in the given image, an X"-axis coordinate and a Y"-axis coordinate in the image coordinate system.

With the image coordinates of the feature points determined, in a next step 54 the image coordinates of each feature point of interest are transformed to the physical coordinate system of the object. Recall that the object image, being a perspective view of the object, contains perspective-view projections of the object features. In this step 54 the perspective-view feature points are deprojected from the image coordinate system to feature points in the physical coordinate system that correspond to an orthogonal view of the features in that coordinate system. This deprojection can be represented as the application of an inverse perspective transformation operator, $P^{-1}$, on the i=1 top feature points of interest of the $j^{th}$ image in the sequence of images, whereby $$j(x_{i=1 \ to \ p}, y_{i=1 \ to \ p}, z) = P^{-1}[j(x''_{i=1 \ to \ p}, y''_{i=1 \ to \ p})] \qquad (2)$$

This inverse perspective transformation operation is carried out, in effect, by first transforming the coordinates of each feature point in the image coordinate system to corresponding points in the viewing coordinate system, and then transforming those corresponding viewing coordinate system feature points to the physical coordinate system. The Z-axis location specified or detected for the feature points is then imposed. These transformations can in practice be carried out in one step, based on the following considerations. Considering the image coordinate system, because the X" and Y" image plane axes are parallel to the X' and Y' viewing coordinate axes, respectively, then for the $i^{th}$ feature point, having coordinates $i(x''_i, y''_i)$, the corresponding viewing coordinates, $i(x'_i, y'_i)$ are given as:

$$x'_i = \frac{x''_i \cdot \Delta_i}{f \cdot k}; \qquad (3)$$

$$y'_i = \frac{y''_i \cdot \Delta_i}{f \cdot k}; \qquad (4)$$

where $f$ is the camera focal length, as described above; k is the camera-specific calibration value described above that specifies, in m/pixel, the distance between the centers of two adjacent pixels of the image acquisition camera; and $\Delta_i$ is given as $\Delta_i = f+d-z'_i$. Here d is the distance of the camera from the Z'-axis origin and $z'_i$ is the projection of the physical coordinate system Z-axis feature plane position, $z_i$, for the $i^{th}$ feature point, to the viewing coordinate system.

Considering the physical coordinate system, the transformation of the $i^{th}$ feature point in the physical coordinate system, $i(x_i, y_i, z_i)$ to the viewer coordinate system as $i(x'_i, y'_i, z'_i)$ is produced as:

$$\begin{vmatrix} x'_i \\ y'_i \\ z'_i \end{vmatrix} = \begin{vmatrix} 1 & 0 & 0 \\ 0 & \cos\theta & \sin\theta \\ 0 & -\sin\theta & \cos\theta \end{vmatrix} \begin{vmatrix} x_i \\ y_i \\ z_i \end{vmatrix}; \qquad (5)$$

where θ is given with reference to FIG. 2 as the angle between the physical coordinate system X-axis and the viewing coordinate system X'-axis. The matrix operation indicated by this expression can be carried out to produce the following representations for the transformation:

$$x'_i = x_i; \qquad (6)$$

$$y'_i = y_i \cdot \cos\theta + z_i \cdot \sin\theta; \text{ and} \qquad (7)$$

$$z'_i = -y_i \cdot \sin\theta + z_i \cdot \cos\theta. \qquad (8)$$

Then substituting expression (8) in expressions (3) and (6) with regard to the X-axis, and substituting expression (8) in expressions (4) and (7) with regard to the Y-axis, the analytical relations to be carried out for the inverse perspective transformation operator, $P^{-1}$, defined above, are given as:

$$y_i = \frac{y''_i(f+d) - z_i(y'' \cdot \cos\theta + f \cdot k\sin\theta)}{f \cdot k\cos\theta - y''_i \sin\theta}; \qquad (9)$$

$$x_i = \frac{x''_i(f+d-y_i \cdot \sin\theta - z_i \cdot \cos\theta)}{f \cdot k}. \qquad (10)$$

These expressions (9) and (10) are implemented for each of the one or more feature points of interest, i=1 to p in the $j^{th}$ image, to transform the set of image coordinate system feature points, $j(x''_{i=1 \ to \ p}, y''_{i=1 \ to \ p})$ to physical coordinate system feature points, $j(x_{i=1 \ to \ p}, y_{i=1 \ to \ p}, z)$ at the Z-axis feature plane position specified or estimated in the previous step 46 for the features of interest. The physical coordinate system feature points represent an orthogonal view of the features in the Z-axis feature plane.

As can be recognized, the coordinate system transformation steps just described can be adapted for various optical conditions of a given application. For example, in an application where the index of refraction is known to change along the line of sight from the image acquisition camera to an object feature plane of interest, then Snell's law relating refractive index with angle of ray direction can be imposed, in the conventional manner, on the transformation expressions at the locations of index changes. With this adaptation, the transformation expressions then will account for diffraction conditions of the application.

In the next step 56 the transformed feature points are correlated with some location in the physical coordinate system if desired for a given application. As can be recognized, for some applications a physical feature-dependent correlation is required, while for other applications a feature-independent correlation may be required, and for yet other applications no specific physical correlation may be needed. The correlation step thus is optional for many applications and is not in general required by the invention.

In one example feature-independent correlation technique, each transformed feature point is correlated with respect to a common physical location, e.g., a known location on the object, a known location in a processing environment, or other location. In one such technique, the location of each feature point of interest is referenced to a location on the object such that the distance of each feature point from the location can be determined. The resulting distance determination can then be employed for later analysis relating to the features.

In an example feature-dependent correlation technique, each transformed feature point is correlated with the specific, feature-dependent physical location of the feature plane to which that point corresponds. In other words, each feature point is associated with its physical orientation on the object. Recall that, as explained above, a sequence of Mobject images represents a series of "snap shots" of the object taken at different angles as if the object were motionless and the camera were moved around the object. Each object image therefore corresponds to a particular object angle that depends on that image's position in the image sequence. But the feature points in each image, as-acquired, are aligned at one and the same object angle with the feature points of all the other images, without regard for the specific object angle that corresponds to a given image in the sequence. In a feature-dependent correlation step 56 each set of image feature points is associated with the correct object angle for those points, and the points are manipulated in a corresponding manner such that the points are correctly oriented with respect to their physical location on the object.

In applications for which knowledge of the physical orientation of features on the physical feature plane is not needed to carry out a desired analysis, e.g., in determination of feature point distance to a reference location that is common or symmetric for all image angles in the image sequence, the correlation of each feature point to its physical location on the feature plane is not required. The correlation step 56 in this scenario can consist of a distance measurement, like that described above, or other feature-independent correlation analysis.

In general, where the object is randomly shaped and the axis of object rotation is randomly located, a feature-dependent, physical location correlation can be carried out using a conventional pattern matching technique in which features of sequential images are compared to correspondingly align the features. The complexity of such a pattern matching technique can be reduced if adjacent images include an overlap of a given object view. Depending on the object image sampling frequency, the rate of object rotation, and other factors, adjacent object images in the image sequence can include redundant object information; in other words, portions of a common view of the object may appear in more than one object image. If feature-dependent location correlation is to be carried out by a pattern matching technique, then it is preferred that some object view overlap be produced. Note also that if there is object overlap between each adjacent object image in the image sequence, then it is assured that an integral image of the entire surface of the object is acquired in one revolution of the object.

For many cases, however, in which the object shape is known, the object's axis of rotation is symmetrical and known, and the features of interest are generally known, feature-dependent location correlation can be carried out as a rotation transformation. Here the set of feature points for the $j^{th}$ object image is rotated by an offset angle referenced to the object orientation for the first image in the image sequence, whereby the correct object angle corresponding to the given set of feature points for the $j^{th}$ object image is imposed. The angular change in image orientation between each of the images in the image sequence is based on the object's period of rotation, $T_0$, and the acquisition period, $T_a$, as $2\pi \cdot T_a/T_0$. Thus, for the $j^{th}$ image, the offset angle, $\lambda_j$, of that image from the initial image orientation reference is given as:

$$\lambda_j = 2\pi \cdot j \cdot T_a/T_0; \tag{11}$$

where j is the index number of the image in the sequence of images. The imposition of this angular offset orientation to the $j^{th}$ image feature point set correlates the feature set with its true physical orientation on the object.

In one example technique for imposing an angular offset on a feature set, each feature point is first translated from its given coordinates in the physical coordinate system to the origin of the physical coordinate system; is rotated by the specified offset angle; and is then translated back to its given coordinates. This three-step operation can be represented as producing an angular offset feature point, $j_{ao}(x_i, y_i)$ by imposition of a forward translation operator, T, a rotation operator, $\Re$, and a reverse translation operator, $T^{-1}$, as follows:

$$j_{ao}(x_i, y_i) = T^{-1} \Re T[j(x_i, y_i), \lambda_j]. \tag{12}$$

The forward translation of a feature point to the origin of the physical coordinate system is produced by imposing on a given feature point the translation operator, T, given as:

$$T = \begin{vmatrix} 1 & 0 & x_i \\ 0 & 1 & y_i \\ 0 & 0 & 0 \end{vmatrix}. \tag{13}$$

The rotation of the translated feature point by the designated offset angle is produced by imposing on the translated feature point the rotation operator, $\Re$, given as:

$$\Re = \begin{vmatrix} \cos\lambda_j & \sin\lambda_j \\ -\sin\lambda_j & \cos\lambda_j \end{vmatrix}. \tag{14}$$

Finally, a reverse translation of the feature point, after its angular offset, is produced by imposing the reverse translation operator, $T^{-1}$, given as:

$$T^{-1} = \begin{vmatrix} 1 & 0 & -x_i \\ 0 & 1 & -y_i \\ 0 & 0 & 0 \end{vmatrix}. \tag{15}$$

All of the feature points of the $j^{th}$ object image are processed based on the translation and rotation operators, whereby the entire feature point set for the image is adjusted to correctly represent its true physical location and orientation on the object.

With the completion of either this feature-dependent location correlation, or with the completion of a feature-independent correlation as described above, an orthogonal view of the features in the image, oriented to the proper object angle if desired, is produced. A next image can then be acquired in the sequence of images to be produced. Referring back to the flow diagram of FIG. 4, in a next step 58 it is determined if a complete sequence of M images has been acquired and analyzed. A conventional counter and comparison technique can be employed to make this determination. If the number, M, of images has been acquired and analyzed, then the process moves to an end step 60. If less than the number, M, of images has been acquired and analyzed, then the loop 48 is continued to acquire and analyze the next $j^{th}$ image in the sequence.

Once all M images are acquired and analyzed, a complete orthogonal view of the object features of interest at the specified Z-axis plane of the object is available for further processing. This further processing, referring back to FIG. 3, can consist of feature analysis for conditions of interest, or other such feature processing. Specific examples of feature processing techniques are described below.

Figures 2, 5:
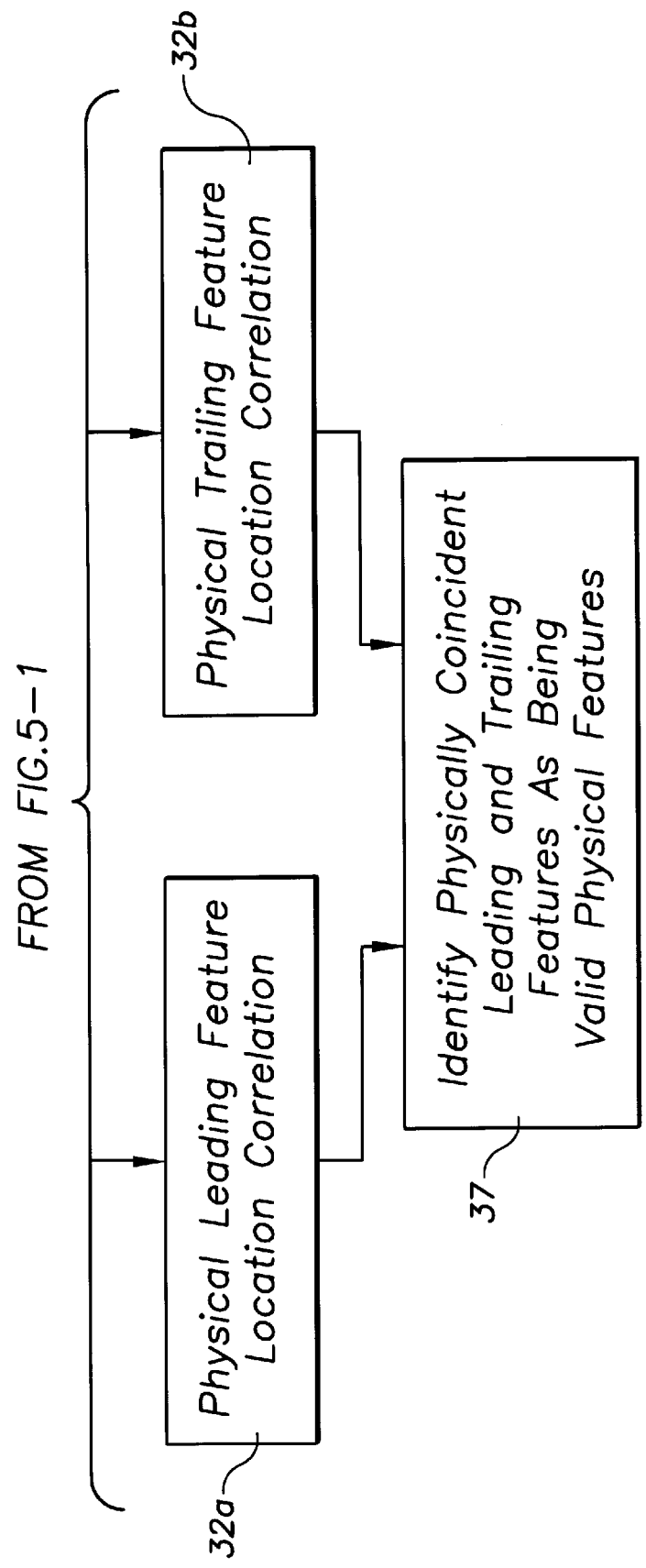
FIG. 5 is a flow diagram of a machine vision technique provided by the invention that is an adaptation of the technique of the FIG. 3 flow diagram, for enabling the validation of features detected in acquired images.

Referring to FIG. 5 there is provided a flow diagram of a machine vision technique that highlights an example implementation of the physical feature validation step in the technique of FIG. 3. Feature validation is provided in accordance with the invention to enhance the ability to carry out valid feature extraction and analysis even in noisy, unpredictable, variable environments. The validation process exploits the premise that either the object under consideration is rotating or the camera acquiring images of the object is being rotated about the object. In either case, a resulting sequence of images of the object consists of snap shots of a field of view into and out of which features of the object are rotated. Thus for a given rotation angle between consecutive acquired images, an object feature is rotated through the field of view from a first position to a second position, i.e., from a leading location to a trailing location in the field of view.

Based on this premise, a leading feature detection location is designated for each image and at least one trailing feature detection location is designated for each image, with the relative positioning of the locations set based on the angle of rotation between consecutive acquired images. Features detected in a given image at the leading feature detection location are then compared with features detected at the one or more trailing feature detection locations in that image of the sequence which corresponds to an object rotation through the angle between the leading and trailing feature detection locations. Features which are found only in one of the leading or trailing feature detection locations are indicative of noise or other invalid representation that is not a true physical object feature. Features which are found in both the leading feature detection location and at least some minimum number of trailing feature detection locations are indicative of object characteristics that are likely to be true physical features of the object.

This validation process can be carried out with one leading feature detection location and one trailing feature detection location, or can employ multiple leading and/or trailing feature detection locations, depending on the degree of validation confidence desired for a given application. In any case, the process provides the ability to validate authenticity of features without the need for a priori knowledge of expected changes in the object or the process environment. Spurious, time-dependent noise or object characteristics typically will appear in only one of the feature detection locations, and are automatically disregarded by the validation process. Characteristics that appear in both leading and trailing feature detection locations are not likely to be time-dependent noise and are accordingly preserved for further feature analysis.

In a first step 26 of the example process of FIG. 5 a perspective-view acquisition of images is carried out, e.g., as in the technique of the flow diagram of FIG. 4. Then in a dual feature extraction process, a leading location feature extraction step 28a is carried out and a trailing location feature extraction step 28b is carried out for each image, either as each image is acquired or after all images are acquired. In this example one leading feature extraction location and one trailing feature extraction location is employed. In the manner of the transformation process described above, a transformation step 30a is then carried out on the extracted leading features and a transformation step 30b is carried out on the extracted trailing features, to transform the feature coordinates from the perspective-view of the acquired image to an orthogonal view of the physical plane in which the features reside.

Then correlation steps 32a, 32b are imposed, if desired, to correlate the transformed leading and trailing features with respect to physical locations on the feature plane. Feature validation is then carried out specifically by an identification step 37 in which physically coincident leading and trailing features are identified as being valid physical features of the object. As explained above, an identification of physically coincident leading and trailing features will be meaningful only if the shift in angle between the leading and trailing edges and correspondingly, consecutive sequence images, is taken into account. With the validation complete, analysis of the features can be carried out with a degree of confidence in the feature data that otherwise would not be had.

As can be recognized, the order of the image acquisition and feature processing steps in the machine vision technique of FIGS. 3–5 can be adjusted without loss of functionality. Preferably, the technique is adapted based on a desired image analysis speed required for a given application. For example, if real time image acquisition and feature analysis is required, then the most computationally-efficient implementation is preferably employed. Computational efficiency is enhanced by maximizing the amount of image analysis applied to a given image rather than to a sequence of images. For example, the implementations of FIGS. 4 and 5, in which each image in the sequence is processed individually in turn, are more computationally efficient than a process in which all Mimages are acquired prior to detection and validation of features in the images. In contrast, if an object under investigation is rotating at a high speed, then an entire image sequence may be acquired prior to detection of features in the images. If off line, rather than real time, feature detection and processing is to be carried out, then computational efficiency is not critical, and processing can be accomplished in a convenient manner.

Other adaptations can also be imposed on the machine vision technique of FIGS. 3–5. For example, the object image view selected for the image acquisition camera can be any selected view, including an orthogonal or a parallel view, and is not limited to an oblique view of any particular viewing angle. The transformation operations described above are an example of a more general association operation contemplated by the invention that associates the feature points of a given image acquisition view with an orthogonal view of the selected feature plane. If the image acquisition view is an orthogonal view of the selected feature plane, then the association task is a simple one-to-one correspondence operation. If the image acquisition view is some non-orthogonal, e.g., perspective view, then the transformation process implements a mapping of the feature points in the perspective view image representation to the desired orthogonal-view feature plane representation.

To acquire images of all sides of the object, the object can rotate about a selected axis of rotation, as described above, or alternatively, the object can be maintained in a stationary position and the camera can be moved around the object. If an entire feature set analysis is not required or if an entire feature set can be viewed with a number of images smaller than that corresponding to a full object rotation, then the object can be rotated only partially through one revolution, or the camera can be moved around only the object sides of interest. In this case, a subset of images, e.g., as little as one or two images, can be employed for feature detection and analysis.

If multiple feature planes are of interest, the object can be analyzed multiple times, each time with a different selected object axis around which the object rotates or around which the camera is moved. The feature plane of interest and the selected object axis can in each case be of a differing orientation, and in general the feature plane of interest does not need to be oriented perpendicular to the axis of rotation. More generally, the feature plane of interest can exhibit slant and tilt with respect to the viewing location as the object rotates, due, e.g., to an oblique orientation of the feature plane with respect to the axis of rotation. In this case, in one example scenario, for each image in the image sequence, a coordinate transformation is imposed on the feature plane based on the degree of slant and tilt and the point of the feature plane that is intersected by the line of sight of the camera. Such a transformation of the feature plane then enables the above feature processing steps to be carried out. A feature plane transformation that accounts for slant and tilt of the plane with respect to a viewing location is provided by Lowell Jacobson in "Conjoint Image Representation and its Application to Viewpoint Invariant Form Recognition and Optical Flow Estimation," University of Minnesota, Ph.D. thesis, 1987.

The feature validation process described above can also be adapted for a range of applications. Validation can be implemented for only a single feature or group of related features of interest to be extracted from each image, or can be implemented to validate a complete set of all features in each image. In some applications, validation may not be required for all features to be detected, in which case a single feature detection location, i.e., not a leading/trailing pair, is preferably configured for each feature not to be validated, and a pair of leading and trailing feature detection locations is configured for each feature or features to be validated. Each pair of detection locations can be associated with a single corresponding feature to be detected or can be associated with multiple features, depending on the configuration of the given application. At one extreme, a single leading and trailing detection location pair is associated with an entire set of expected features, while at the other extreme, a single leading and trailing detection location pair is associated with a single feature. Thus, multiple pairs of leading and trailing feature detection locations can be configured for simultaneously carrying out multiple and distinct feature validation operations.

As explained earlier, for each pair of leading and trailing feature detection locations, the two locations in the pair are configured with respect to each other such that a feature of interest appearing in the first of the locations in one image later appears in the second of the locations in the other image. The detection location configuration is thus based on an expected shift of the feature between the images. The feature shift can be a linear translation, an angular rotation, a combination of rotation and translation, or some other progression of the feature location.

In a further adaptation of the validation process, a single feature can be associated with multiple feature detection locations, configured not as pairs but as a related set of detection locations. In this scenario, multiple feature detection locations can be configured in a spatial relation that corresponds to a series of consecutive images in the image sequence. For example, a number, n, e.g., four, detection windows can be configured in a spatial relationship with respect to each other, corresponding to the expected location of an object feature as it will appear in four consecutive images of the image sequence. Here detection of the feature in some minimum number of the n detection windows through the sequence can then be employed as a validation operator. The set of detection windows need not be configured for analysis based on a consecutive series of images; instead, images set apart in the image sequence by a specified number of intermediate images can be considered. Here the detection locations are spaced relative to each other based on the shift of the object feature between two consecutive images, multiplied by the number of intermediate images to be designated. This configuration based on spaced-apart images in the sequence can equally be applied to a single leading and trailing detection location scenario. As can be recognized, this technique further can be extended to an exhaustive image analysis operation in which the complete physical plane in the image is fully reconstructed, not just selected edge points. Individual features in the reconstructed plane can then be extracted with conventional techniques such as a boundary tracking operation.

As can be recognized, other adaptations of the technique are contemplated by the invention. For example, the feature point transformation steps described above can be imposed on an entire image coordinate system instead of on particular feature points themselves. In one example of this scenario, the image coordinates are transformed to corresponding physical coordinates prior to detection of features in the image. Then, when features points are detected in the image, the locations identified in the image as being associated with detected feature points are automatically referenced to the physical coordinate system, and a separate feature point transformation step is not required. In a further adaptation, correlation of the transformed image coordinates with respect to, e.g., some common physical location, or to their corresponding physical orientations on the feature plane, can be carried out prior to the step of identifying feature points in the images. Here each image can be transformed and correlated for carrying out feature point identification in each image, or alternatively, the transformed images can be averaged in the transformation process to produce an average transformed image in which feature points are identified. In a further alternative technique, one acquired image can be transformed to the physical coordinate system, correlated to its physical orientation on the feature plane, and then transformed back to the image coordinate system. Then the other acquired images can be correlated in the image coordinate representation, rather than the physical coordinate representation, to their physical orientations, based on the image representation of the first transformed and correlated image. Correlation can thus be accomplished in any desired coordinate system representation with the appropriate correspondence to the physical coordinate system provided in some manner. Other such adaptations can be accommodated.

Figure 6:
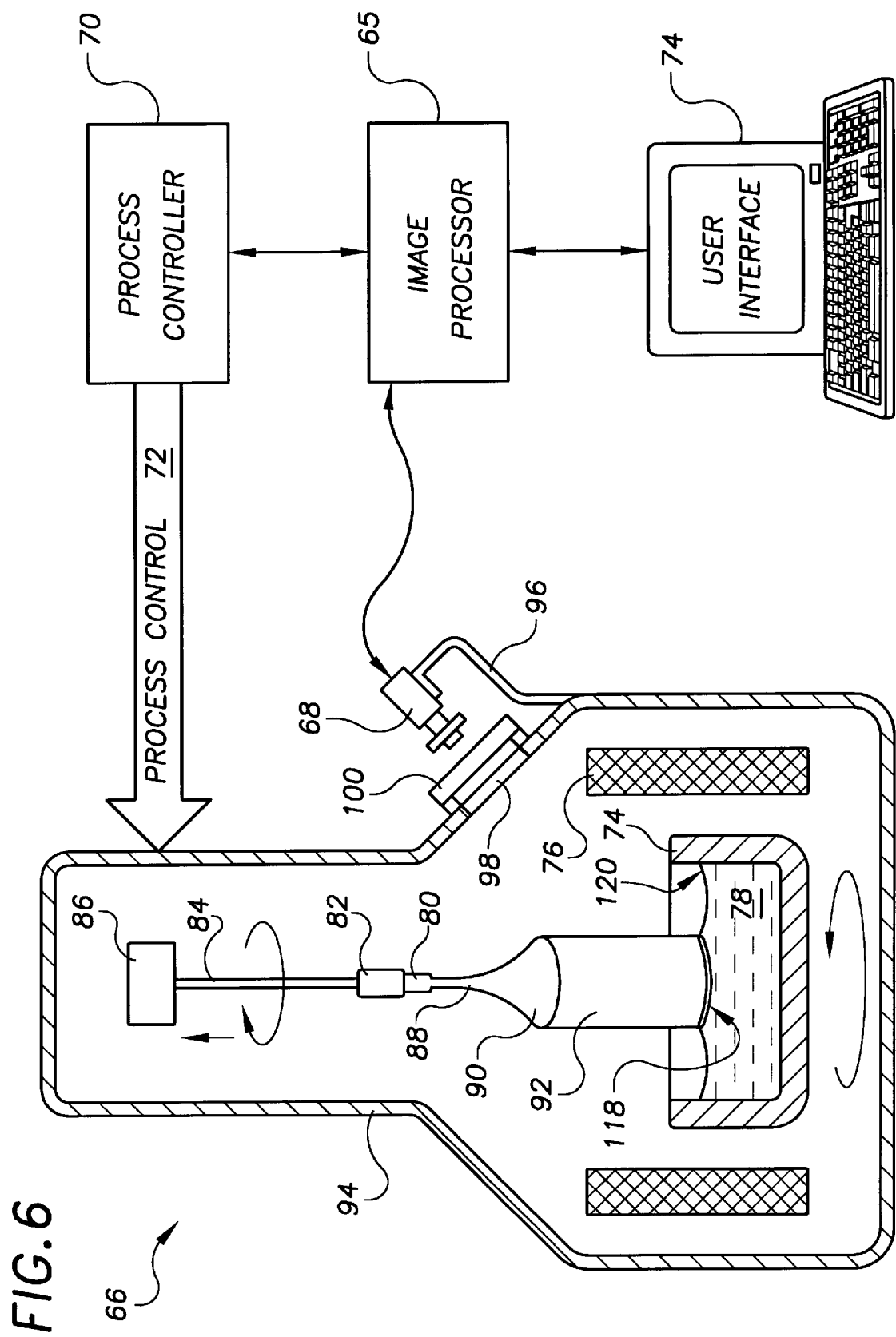
FIG. 6 is a schematic representation of a semiconductor crystal ingot growth apparatus and of a machine vision image processor provided by the invention for monitoring the growth apparatus using the machine vision techniques provided by the invention.

Referring to FIG. 6, there is shown an example implementation of a machine vision image processor 65 configured in accordance with the invention for a machine vision application requiring acquisition of multiple object images to detect, validate, and analyze a set of object features. The example application here is the monitoring and control of a semiconductor crystal growth apparatus 66 and its operation. The image processor 65 processes images acquired from an image acquisition camera 68 and based on the image processing, directs a process controller 70 to signal process control 72 to the crystal growth apparatus. A user interface 74 is provided for input of image process parameters and for output of the image processing results to the user.

Virtually all electronics-grade single crystal semiconductor wafer production, e.g., silicon and gallium arsenide wafer production, is accomplished using an apparatus like that shown in FIG. 6, for carrying out the well-known Czochrolaski crystal growth technique. In the Czochrolaski crystal growth technique, for, e.g., growth of a silicon ingot, a crucible 74 of electronic-grade silicon pieces is heated using, e.g., an annular radiant heating mechanism 76, to produce a silicon melt 78. A single crystal seed crystal 80, mounted in a crystal chuck 82, is dipped into the melt and then slowly pulled upward as both the crystal and the crucible are rotated, in opposite directions, to enable the condensation of the melt onto the seed crystal in the crystalline structure of the seed crystal. A cable 84 supported from a cable controller 86 draws the growing crystal upward and rotates the crystal. A crucible controller (not shown) rotates the crucible in a direction opposite that of the crystal. As the crystal growth progresses, a neck 88, crown 90, and body 92 of a silicon ingot, or boule, is produced. Once a complete ingot has been grown, the ingot is then sliced into wafers for further processing, e.g., monolithic circuit fabrication.

The silicon ingot growth process is expensive and susceptible to process error, and thus requires constant monitoring to ensure satisfactory process progression. Because the process typically must be carried out under vacuum or in an inert atmosphere to suppress impurity absorption into the silicon, and due to the high temperature of the silicon melt 78, the apparatus is typically housed in a secure housing such as a steel-walled chamber 94. As a result, a process operator does not have direct access to the process and cannot use tactile monitoring techniques.

In accordance with the invention, an acquisition camera 68 is secured by, e.g., a bracket 96 such that the camera is oriented over an optical view port 98 of the chamber 94. Typically only a single such view port 98 is provided as the single optical access point to the silicon growth process, and generally includes a heat shield 100 for protecting the observer from the high temperature internal to the chamber. Note that due to the configuration of the growth crucible and annular heater, the melt, and the vertical ingot pulling apparatus, the view port can generally only be located, as a practical matter, at a point along the chamber that provides a perspective view of growing ingot and the melt. A side or top-down view of the process is not possible. The perspective-view image acquisition and analysis techniques provided by the invention enable a robust, automated, and real time machine vision monitoring of the crystal growth process while accommodating the oblique process view provided by the single chamber view port. The machine vision monitoring process is found to provide process control in a manner that is more efficient and responsive than could be expected from human operator monitoring.

Figure 7:
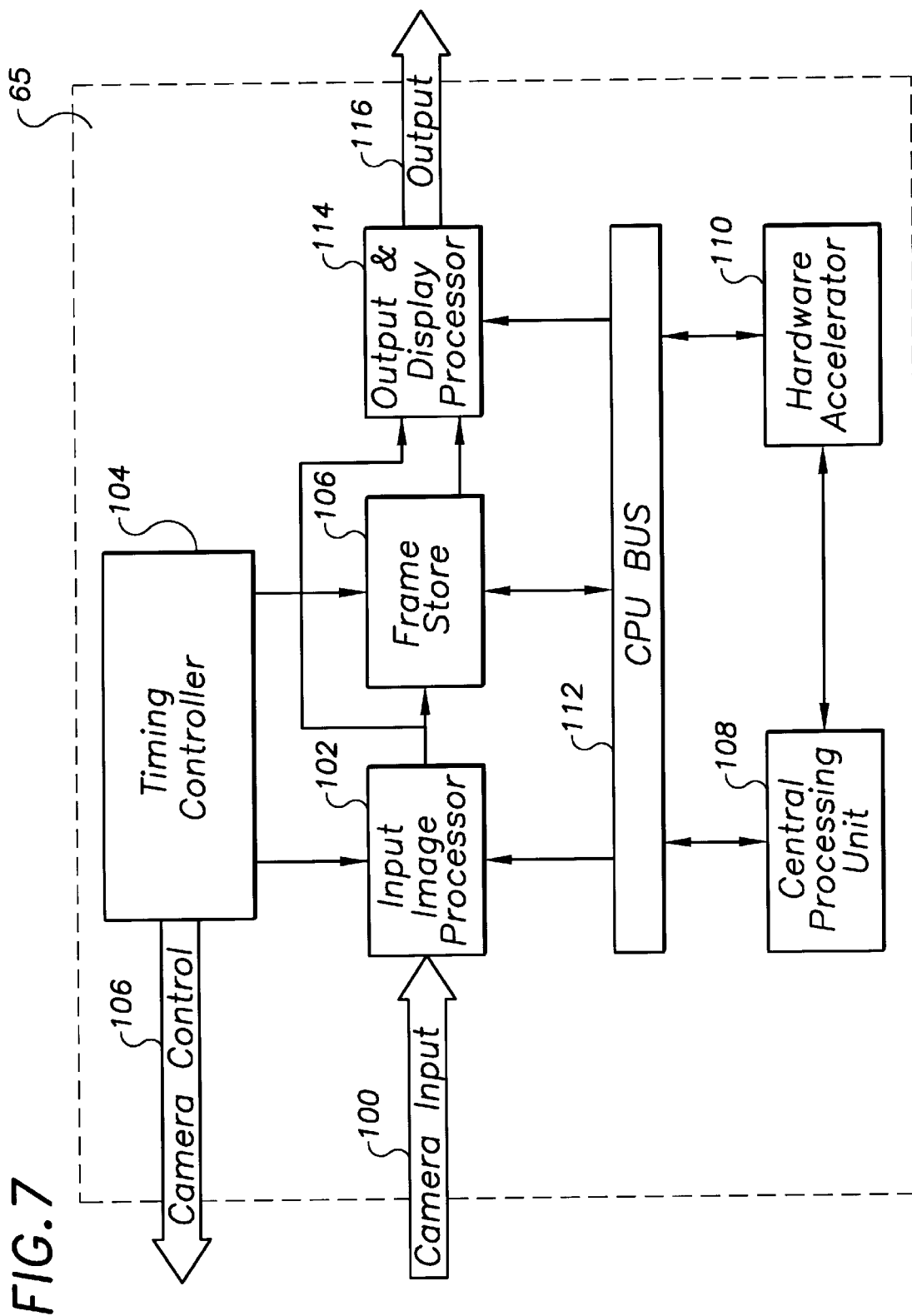
FIG. 7 is a block diagram of the components of the image processor of FIG. 6 as provided by the invention.

Referring also to FIG. 7, there is shown an example configuration of the image processor 65 provided by the invention for carrying out the image acquisition and analysis technique of FIG. 3 for, e.g., monitoring the silicon growth process of FIG. 6. Input 100 from the image acquisition camera is directed to an input image processor 102. A timing controller 104 directs the operational timing of input image processor 102 and provides timing camera control 106 to synchronize the image acquisition operations of the camera with the processor operations. Preferably the camera is implemented as a general purpose video camera such as the XC75 CCD camera available from Sony Corp.

The input image processor accepts the camera input in the form of analog signals, conditions the signals, e.g., by applying gain and offset levels, to compensate for particular process conditions, and then digitizes the signals. The resulting digitized signals are pixel intensity value representations that are formatted as rows of pixels in image frames. As the pixel intensity data is produced it is stored in a frame store 106 for access by a central processing unit (CPU) 108 and optional hardware accelerator 110 to carry out the image and feature analysis. User input, e.g., expected vertical location of the ingot-melt meniscus, from the user interface, is input to the CPU for control of the image analysis. A CPU bus 112 provides both data and control signal communication between the various processing modules, as shown. If the CPU is not implemented as a relatively high-speed processor, e.g., as a Pentium™ processor from Intel, Corp., then a customized hardware accelerator 110 is preferably included to enable a speed of image analysis that accommodates real time process monitoring and control. If real time process monitoring and control is not required, then a relatively slower processor can be accommodated.

Once the image and feature analysis is complete, the resulting image data is directed from the CPU 108 and optional hardware accelerator 110, via the CPU bus 112, back to the frame store 106. This processed image data, as well as input image data from the input image processor 102, is directed to the output and display processor 114. The output and display processor 114 creates an analog video signal corresponding to the digital image data, and produces an output 116, e.g., a display drive output, for displaying the analog video signal on a user interface monitor. The analog signal can be created based on real time input image data, frame store image data, or various combinations of real time and stored image data, depending on the analysis being carried out and the requests of the user. The timing controller synchronizes the camera input 100 with the processing operations and the processor output 116 to maintain a known regulated time sequence of image data.

One suitable commercial image processor that can be configured to carry out the image acquisition and analysis techniques of the invention is the 4400 Vision Processor Board and accompanying software from the Cognex 4000 Series Vision System available from Cognex Corp., of Natick, Mass.

Referring back to FIG. 6, the user interface can be provided as a conventional computer, including, e.g., a screen and keyboard, or can be configured as a memory storage unit, printer unit, or other communication mechanism. The user interface can be remote from the processor, connected by, e.g., a shared-bus, a local area network, a wide area network, a wireless network, or other communication scenario. Similarly, the image processor can be located remotely from the image acquisition camera, with communication between the two effected by wire or wireless network, for example.

As can be recognized, the image processor can be configured in various scenarios based on the application environment. For example, given multiplexing/demultiplexing capabilities, the processor can be configured to monitor several crystal growth processes simultaneously. The processor can be implemented using commercially-available hardware such as that described above, or can be implemented entirely in customized hardware, alternatively implemented on a general purpose computer system with corresponding software, or alternatively implemented on a suitable combination of hardware and software components that accommodates demands of a given application.

Referring back to FIG. 6, the image processor and image analysis techniques provided by the invention find many specific applications in the crystal growth example presented. Real time and automatic monitoring of the apparatus enables the detection of growth conditions that could indicate a fault in the process conditions or a defect incorporated in the crystal ingot. An important example of such monitoring is the inspecting of the crystal melt surface for the appearance of solid phase crystal nucleation and crystallization, known as melt surface "ice."

Briefly, ice can form on the surface of a melt, such as a molten silicon melt, if the temperature of the melt surface drops below the temperature required to maintain the crystalline material in the molten state. Ice can nucleate at the boundary of the growing crystal ingot on the melt surface as well as at the boundary of the melt crucible and the melt surface. Once ice nucleation is initiated, a solid ice layer quickly forms across the melt surface. Eventually the solid ice layer completely covers the melt surface and produces a solid bridge between the growing ingot and the melt crucible. Because the ingot and the crucible are rotated in opposite directions during the crystal growth process, this ice bridging can result in catastrophic damage to the crystal growth apparatus as well as destruction of the growing ingot. Early detection of surface ice formation is thus critical to successful crystal growth.

Given the nucleation of a surface ice layer at either or both the crystal ingot and at the melt crucible, an annulus of ice-free melt surface exists but tends to be rapidly covered by any ice growing inward from the crucible and any ice growing outward from the ingot. The larger the ice-free melt surface annulus at the time of ice detection, the more time is available to a process operator to salvage the growing ingot and save the growth apparatus from damage. Specifically, the operator tries to raise the ingot out of the melt before the ice bridges between the ingot and the crucible. As a practical matter, ice nucleation initiated at the ingot destroys the usability of the entire ingot. This is due to a requirement for growth of a cone-shaped ingot end face to preserve the crystallinity of the ingot; abrupt withdrawal of the ingot from the melt cannot produce this cone. Thus, when ice nucleation is detected at the ingot, the ingot is just quickly raised out of the melt to prevent damage to the crucible. However, if ice nucleation is found to have initiated at the crucible but not at the ingot, then the process operator may be able to successfully grow the required cone-shaped ingot end face before the ice bridges from the crucible to the ingot. In this case it is optimal that the operator be alerted to the detection of ice nucleation at the crucible at the earliest possible time. The larger the ice-free annulus of melt at the time of detection, the longer a usable ingot can be grown.

Early ice detection can only be reliably achieved with constant monitoring of the molten melt surface as the ingot growth process is carried out. But the limited and oblique viewing port of the crystal growth chamber can impede the ability to recognize the initial stages of nucleation even when constant attention is given to the monitoring. Distraction, fatigue, inexperience, and other human factors further limit the ability to quickly detect initial ice nucleation. Operator monitoring for the initiation of ice nucleation is thus found to not provide a degree of safeguard against ice damage that is commensurate with the very high costs associated with such damage.

Figures 8A, 8B:
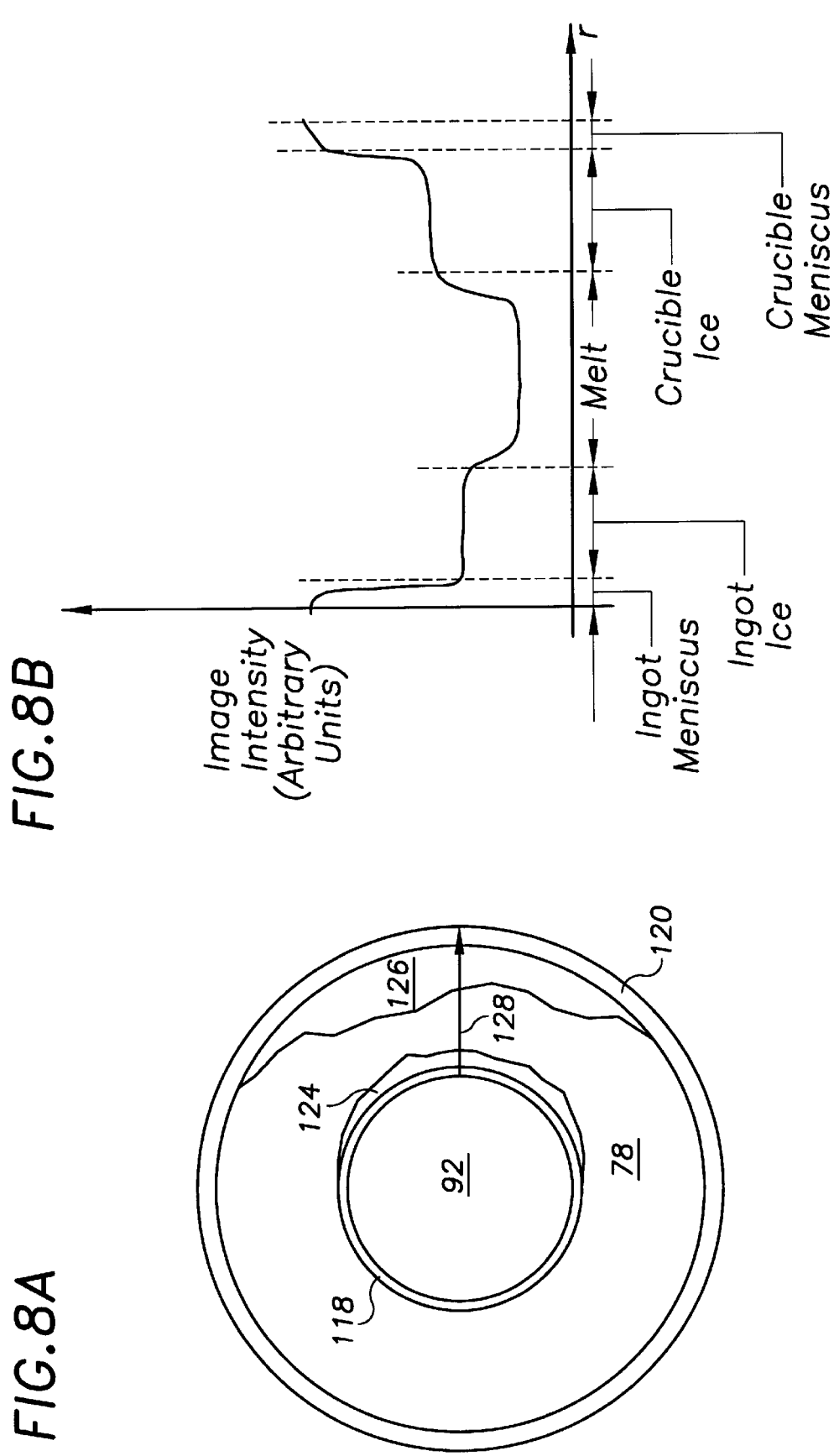
FIG. 8A is a schematic representation of a top-down, cross-sectional view of a growing crytal ingot being pulled out of a melt in a crucible, with surface melt ice forming at the ingot and at the wall of the crucible.
FIG. 8B is a plot of an image intensity profile of the top-down view of FIG. 8A, moving outward along a path taken from the ingot to the crucible.

Referring to FIG. 8A, there is shown an optimal ice detection viewing configuration, consisting of an orthogonal, top-down cross-sectional view of a crystalline melt surface 78 and a crystal ingot 92 being raised out of the melt. The interface between the ingot and the melt appears optically as an ingot meniscus 118 and the interface between the crucible and the melt appears optically as a crucible meniscus 120. Referring back to FIG. 6, the ingot meniscus 118 and the crucible meniscus 120 both arise due to surface tension of the liquid melt on the ingot and the crucible. As shown in FIG. 8A, a developing surface layer of ingot ice 124, i.e., ice formation that was initiated at the ingot, constitutes a contour that originates and terminates at an interface with the ingot. Similarly, a developing surface layer of crucible ice 126, i.e., ice formation that was initiated at the crucible wall, constitutes a contour that originates and terminates at an interface with the crucible. As the ingot ice formation grows, such can completely encircle the ingot, and as the crucible ice formation grows, such can completely surround the crucible circumference, thereby in each case forming a closed contour that does not terminate at the ingot or crucible, respectively.

This orthogonal top-down view of the ingot growth process provides a distinctive image intensity profile that can be directly related to the ice formation condition of the growth process at any given time during the process. Specifically, given an imaginary radial path 128 take from the ingot meniscus 118 to the crucible meniscus 120 and along which an image intensity profile is captured, distinct image intensities are found to be associated with each of the ingot meniscus, ingot ice, liquid melt, crucible ice, and crucible meniscus, and distinct image intensity transitions are found to occur at each interface between these physical regions.

Referring also to FIG. 8B, in an image intensity plot corresponding to the captured intensity profile along the radial path in FIG. 8A, it is found that typically the surface of an ice region is brighter in intensity than the molten melt, and darker in intensity than the meniscus at the ingot and the meniscus at the crucible. The two meniscuses thus exhibit the highest intensity along the profile and the melt exhibits the lowest intensity along the profile. The ingot-related and crucible-related ice regions exhibit intensities lower than that of the meniscuses and higher than that of the melt.

With this distinctive image intensity profile, it is found that ingot-related ice is associated with a negative image intensity transition, i.e., a transition to lower intensity, moving from the ingot meniscus to the ingot ice, and correspondingly, that crucible-related ice is associated with a positive image intensity transition moving from the crucible ice to the crucible meniscus. Moving from the ingot ice to the melt, a negative intensity transition is encountered, and moving from the melt to the crucible ice, a positive image intensity transition is encountered. With this profile directionality, An ingot-related ice region can thus be defined as a region bounded by the negative ingot meniscus-to-ingot ice intensity transition and the negative ingot ice-to-melt intensity transition. A crucible-related ice region can similarly then be defined as a region bounded by the positive melt-to-crucible ice intensity transition and the positive crucible ice-to-crucible meniscus intensity transition.

The invention exploits this distinctive image intensity transition profile to provide an automatic machine vision technique for detecting the presence of ingot ice and/or crucible ice during the crystalline growth process based on the intensity transition profile of the process. The technique further exploits the machine vision processes described above to transform a sequence of acquired perspective-view images of the process, taken through the perspective-view port of the process chamber, to a corresponding orthogonal-view image of the process, whereby a top down, cross-sectional, orthogonal-view like that of FIG. 8A can be provided. This optimal view then can be analyzed for producing the requisite image intensity transition profile that relates to the physical spatial configuration of the growth process regions. The limitations of the perspective angle viewing port of the crystal growth apparatus are thus overcome by the machine vision technique to enable an optimum image configuration and corresponding image analysis.

Referring back to FIG. 6, several considerations must be made with regard to the complicated arrangement of the crystal growth apparatus. Given image acquisition by an acquisition camera 68 positioned above a perspective-view port 98 in the growth chamber, the entire surface of the melt 78 and ingot 92 cannot be seen in a single image, due to both occlusion by the ingot of portions of the melt and the typically small size of the viewing port. But because both the ingot and the crucible are rotated during the process and any ingot-related and crucible-related ice also rotate with the respective ingot or crucible to which they are connected, a sequence of viewing port images taken during one full revolution of both the ingot and the crucible provides all information necessary to reconstruct the desired orthogonal view of FIG. 8A based on the techniques of FIGS. 3–5 above.

A further complication for the image analysis is caused by the opposite rotations of the crucible and the ingot. Specifically, the correlation and transformation of detected features relating to the crucible and its ice require operations distinct from the correlation and transformation of detected features relating to the ingot and its ice. As a result, image analysis of the crucible ice must be carried out separately from that of the ingot ice. The partitioned nature of the analysis operations thereby enables the implementation of either or both the ice detection operations for a given application.

Figures 1, 9:
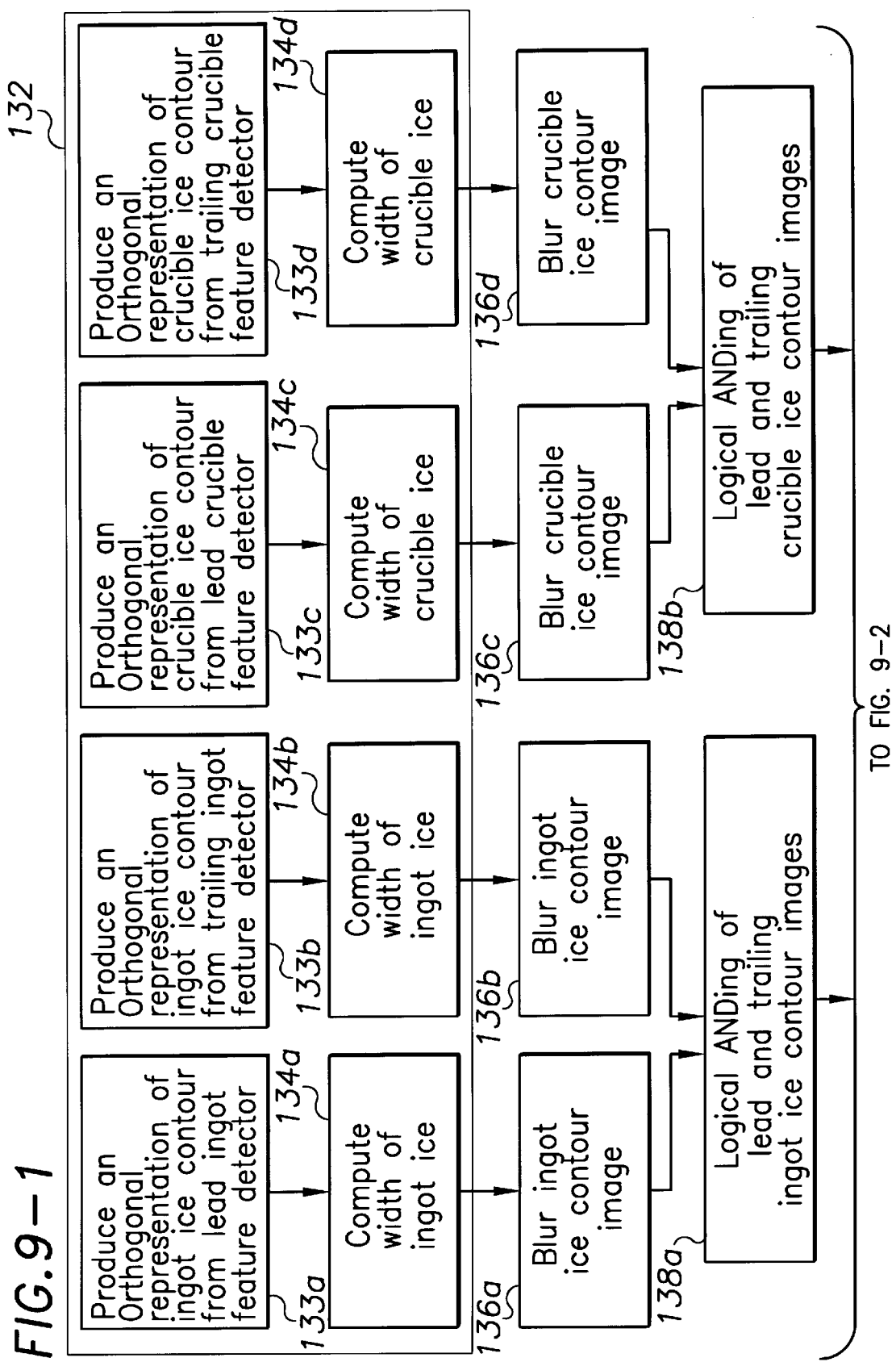
FIG. 9 is a flow diagram of a machine vision technique provided by the invention for monitoring a semiconductor crystal ingot growth process environment to determine if melt surface ice has formed at the ingot or the crucible wall.
Figures 2, 9:
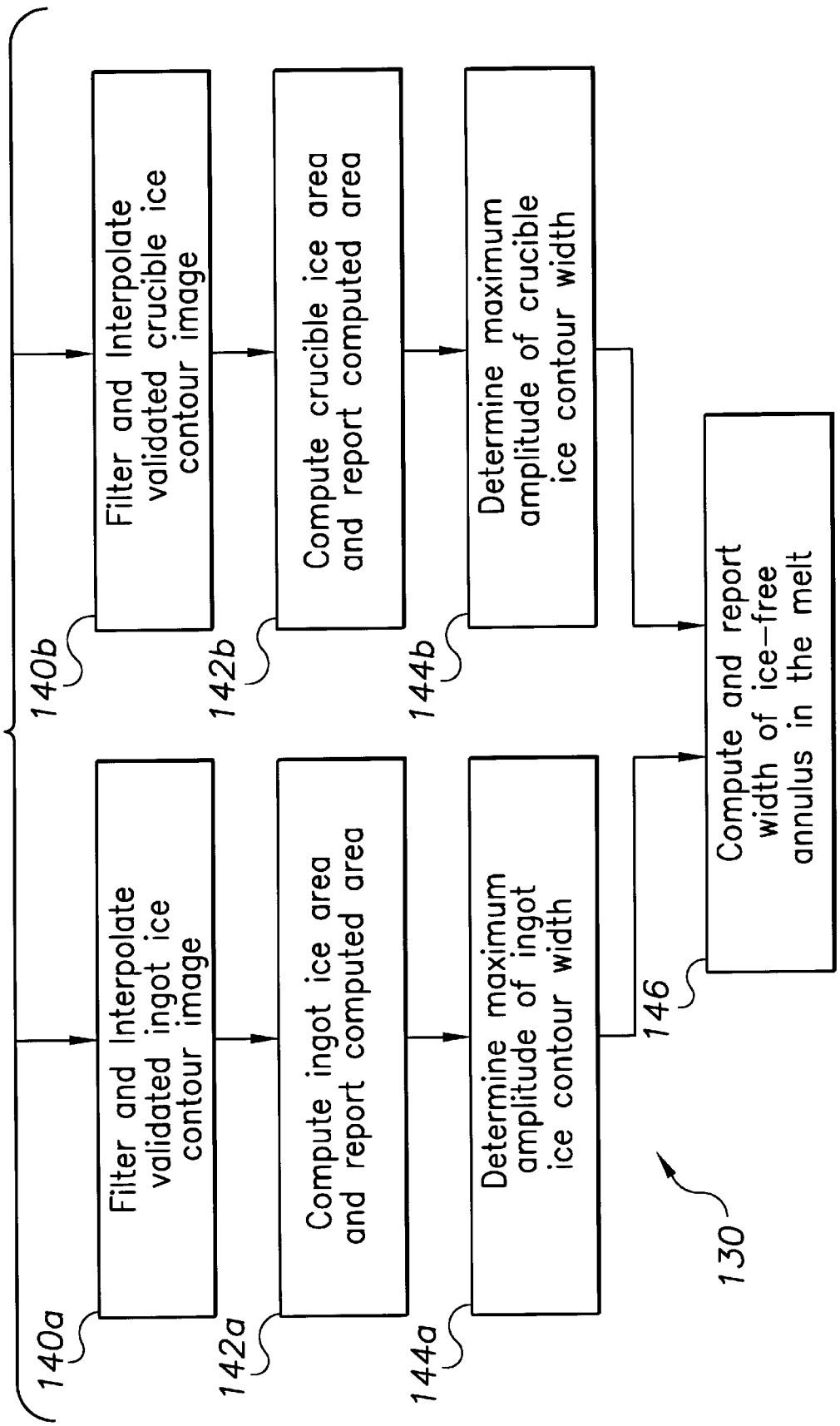

Referring to FIG. 9, there is provided a flow diagram of an ice detection technique 130 in accordance with the invention and as an example application of the techniques described above with regard to FIGS. 3–5. This example is adapted to detect both ingot ice and crucible ice. This example is further adapted to validate ice features detected by the process using a lead and trailing feature detector pair configured for detection of ingot ice and a lead and trailing feature detector pair configured for detection of crucible ice, both in the manner described above. With this adaptation of the technique, in a first step 132 an orthogonal image representation of an ingot ice contour, if ingot ice is found, and a crucible ice contour, if crucible ice is found, are produced based on image acquisition and feature extraction operations from the corresponding feature detector pairs, as described in detail below. This step thus consists of four processes 133a–133d producing lead and trailing ingot ice contour images and lead and trailing crucible ice contour images. Each of the ice contour images correspond to the top-down cross-sectional and orthogonal view of FIG. 8A, relating to the physical plane of the melt surface. In this first step 132 is also carried out four computation functions 134a–134d to determine the width of the each of the ingot and crucible ice regions for which the four ice contour images have been produced.

Next is carried out an optional machine vision blurring step 136a–136d, applied to each of the four ice contour images, to compensate for extraneous noise in the detection process, as described in detail below. The lead and trailing ingot ice contour images and the lead and trailing crucible ice contour images are then separately processed as pairs in logical ANDing steps 138a, 138b, to produce a validated ingot ice contour image and a validated crucible ice contour image. As explained in detail below, this validation step compensates for unpredictable variations in the process images, e.g., variability in the images' intensity profiles, extraneous noise introduced into the image acquisition process, and other nonideal process conditions.

Given a validated ingot ice contour image and a validated crucible ice contour image, the two contours are separately processed in filtering and interpolation steps 140a, 140b to further remove noise from the images and to bridge any gaps in the contour profiles. With filtered, continuous profiles thus produced, in next process steps 142a, 142b the ingot ice area is estimated and the crucible ice area is estimated, or some index directly related to the ice area is computed; and if desired, the area estimation and/or area index is reported to the process operator for consideration. The maximum amplitude point of the ingot ice contour width and the maximum amplitude point of the crucible ice contour width are then computed in proceeding steps 144a, 144b.

In a final step 146, the maximum ingot ice width and the maximum crucible ice width are employed to ascertain the width of the ice-free annulus in the melt between the two ice formations. In other words, here is determined the span of the melt surface that is not covered by ice when the widest section of the ingot ice passes the widest section of the crucible ice as the two rotate in opposite directions. This ice-free annulus width is reported to the operator for consideration of timing in carrying out emergency procedures to remove the ingot from the melt and prevent catastrophic damage to the crucible.

Figures 1, 10:
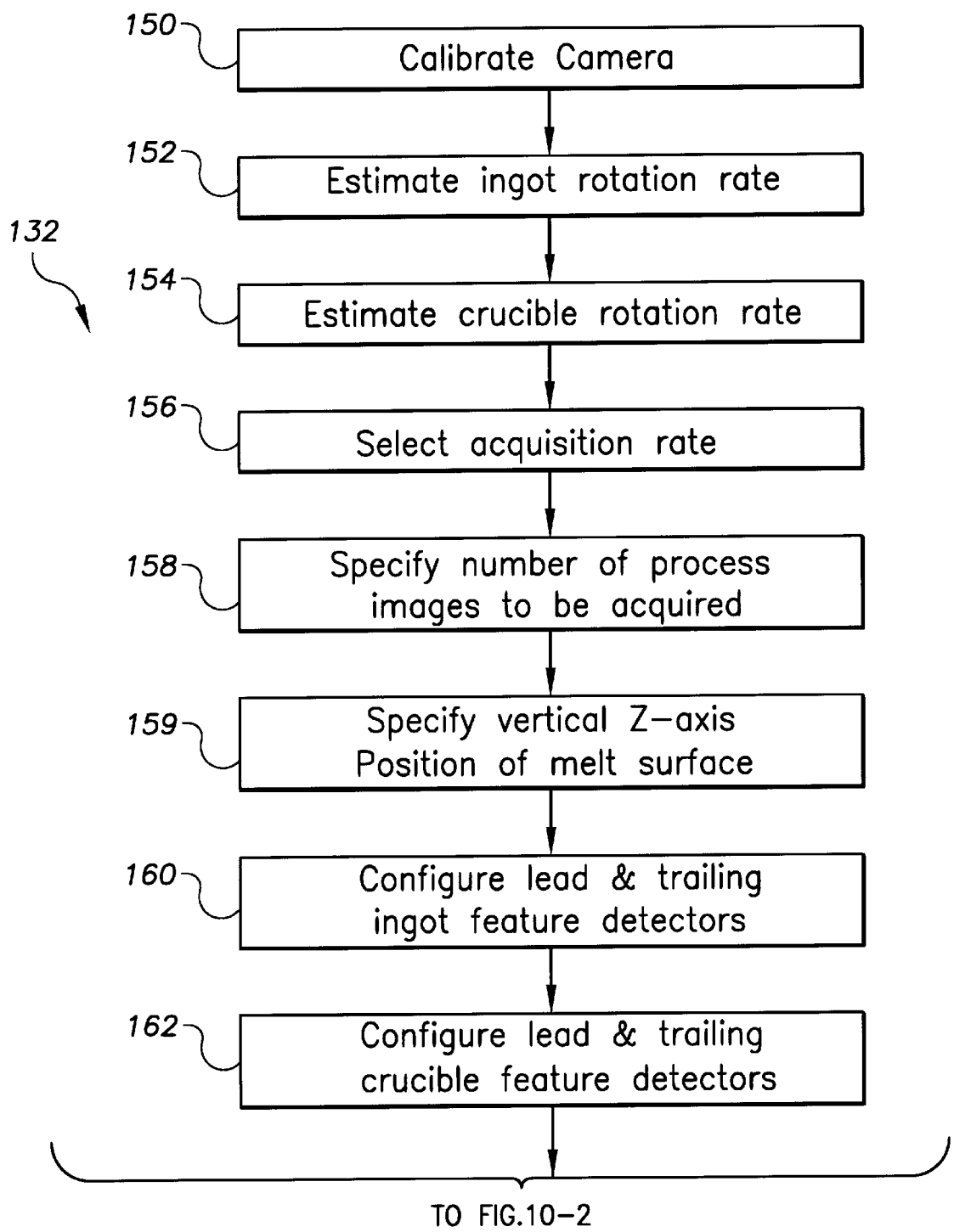
FIG. 10 is a flow diagram of a machine vision technique provided by the invention for carrying out the ice contour image production and analysis that is first step of the flow diagram of FIG. 9.

Considering the ice detection steps in more detail, with regard to the first step 132 of producing an orthogonal representation of lead and trailing ingot ice contours and lead and trailing crucible ice contours, specific processes for carrying out this step are shown in the flow diagram of FIG. 10. In a first step 150, corresponding to that of the flow diagram of FIG. 4, the image acquisition camera is calibrated based on the orientation of the growth chamber view port with respect to the surface of the crystal melt. The physical, viewing, and image coordinate systems of FIG. 2 are thus configured for the camera position in the chamber view port. In next steps 152, 154 the rotation rate of the ingot and the rotation rate of the crucible are ascertained, respectively. The rotation rates can be ascertained from data supplied by the growth process control computer, if available, or can be determined experimentally using conventional techniques such as encoder sensing.

In a next step 156 is selected the rate at which images are to be acquired by the image acquisition camera. As explained earlier, the image acquisition period, $T_a$, corresponds to the acquisition rate at which the camera can operate, and is a function of the finite amount of time required by a given camera to physically produce an image of a scene. In this step the acquisition rate and corresponding acquisition period that is required for the selected acquisition camera, given the lighting conditions of the growth chamber, is specified.

In a next step 158 the number, M, of total images to be acquired for carrying out the ice detection process of FIG. 9 is determined. Preferably, the acquired image sequence includes views of at least one complete revolution of both the crystal ingot and the melt crucible. Accordingly, images are acquired for at least one period of revolution of both the crystal ingot and the melt crucible. Given that only one image sequence is employed to capture views of both the rotating ingot and the rotating crucible, the image sequence should preferably be acquired for a time period corresponding to the longer of the rotation period of the ingot and the rotation period of the crucible.

The ingot rotation period, $T_{ingot}$, is computed as $1/\omega_{ingot}$, where $\omega_{ingot}$ is the rotation rate of the ingot; and the crucible rotation period, $T_{crucible}$, is computed as $1/\omega_{cruible}$, where $\omega_{crucible}$ is the rotation rate of the crucible. Given the image acquisition period, $T_a$, described above, the number, M, of images to be acquired in an image sequence that provides views of a complete revolution of both the ingot and the crucible is then given as $$M = n \frac{\max(T_{ingot}, T_{crucible})}{T_a}; \tag{16}$$

where n≧1 and max($T_{ingot}$, $T_{crucible}$) is refers to the longer of the two rotation periods. This ensures that 360° views of both the ingot and the crucible are obtained in the acquired sequence of images.

In a next step 159 the vertical Z-axis melt location is specified. This can be determined based on the Jacobson description, previously referenced, in U.S. Ser. No. 08/758,426, filed Nov. 29, 1996, entitled "Vision System For Estimating a Radius Profile of a Solid-Of-Revolution," assigned to the assignee of the present invention, and incorporated by reference. Appendix A also provides an outline of the steps in determining the Z-axis melt location. The physical melt location on the Z-axis is required for configuring feature detectors with coordinates in the acquired images.

It is in the next step 160 that the lead and trailing ingot feature detectors are configured with respect to the coordinate system of the perspective view images to be acquired, such that ingot-related ice can be detected. This is accomplished in one example technique provided by the invention by specifying image detection locations at which the ingot meniscus and ingot ice contour points are expected to be positioned. An edge detection tool such as the Caliper Tool from Cognex Corporation referenced above can be employed to impose lead and trailing edge detection regions on the acquired images at the expected ingot meniscus and ingot ice contour point locations. In a similar manner, in the next step 162 lead and trailing crucible feature detectors can be configured to detect crucible-related ice.

Figure 11:
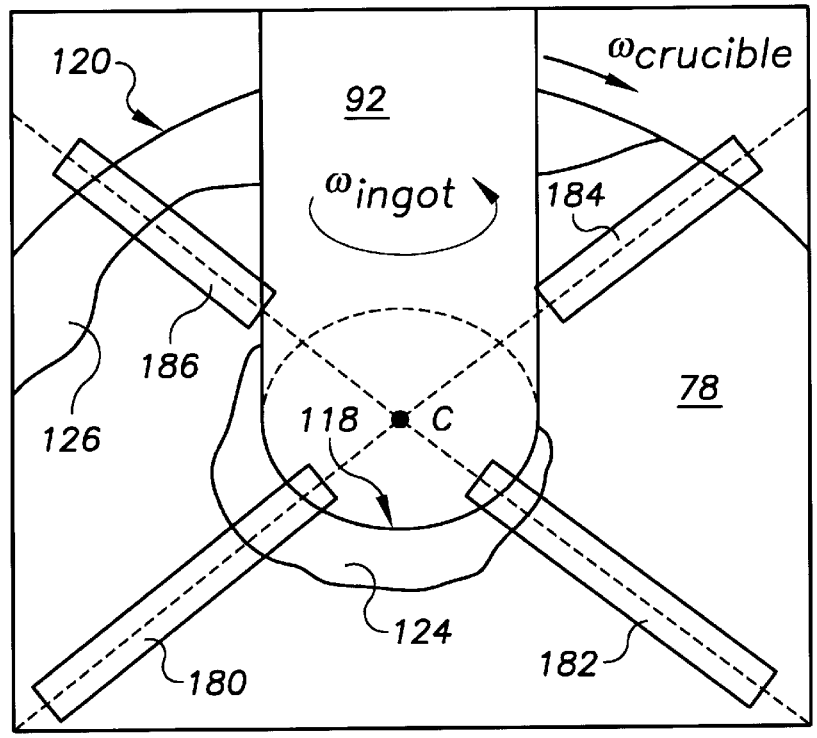
FIG. 11 is a schematic representation of an acquired perspective-view image of a growing crytal ingot being pulled out of a melt in a crucible, including surface melt ice forming at the ingot and at the wall of the crucible, with lead and trailing feature detectors configured to detect the ingot ice and the crucible ice.

Referring to FIG. 11, in an example perspective-view image of the ingot growth process, it is found that typically the image's field of view is not large enough to capture the entire diameter of the melt 78. To accommodate this condition, in one example configuration, the ingot 92, the ingot meniscus 118, and any ingot-related ice 124 is captured in the foreground of the image, while the crucible meniscus 120 and any crucible-related ice 126 is captured in the background of the image. A lead ingot ice detector 180 and trailing ingot ice detector 182 are to be configured with respect to the image coordinates to capture features relating to the ingot ice, and similarly, a lead crucible ice detector 184 and trailing crucible ice detector 186 are to be configured with respect to the image coordinates to capture features relating to the crucible ice. Each detector in the pair is designated as the lead or the trailing detector based on the direction of rotation of the ice or crucible; the directions of rotation shown in the figure designates the detectors as given above.

In an optimal configuration, the ingot ice feature detectors 180, 182 are each configured as a rectangle lying along a radial path emanating from the ingot center point, with the radially-innermost edge of the rectangle positioned within the radial span of the ingot and the radially-outermost edge extending as close to the image boundary as possible, as shown in FIG. 11. Similarly, the crucible ice feature detectors 184, 186 are each optimally configured as a rectangle lying along a radial path emanating from the ingot center point, with the radially-outermost edge of the rectangle positioned outside of the radial span of the crucible and the radially-innermost edge extending to the ingot meniscus, as shown in the figure. It is preferred that the detectors be configured along radial lines such that a radial image intensity profile like that of FIG. 8B can be produced based on the features extracted by the detectors.

To enable this configuration of the feature detectors, in one example process, there is first determined the radius of the ingot meniscus 118 in the physical coordinate system as it projects from the location of the center point, C, and there is determined the radius of the crucible meniscus 120 in the physical coordinate system. This can be accomplished using a priori knowledge of the ingot and crucible provided by the growth apparatus controller or assumptions made regarding the growth configuration, or can be detected as the growth is carried out.

A preferred technique for determining the ingot and crucible meniscus radius is described by Lowell D. Jacobson in U.S. Ser. No. 08/758,426, filed Nov. 29, 1996, entitled "Vision System For Estimating a Radius Profile of a Solid-Of-Revolution," assigned to the assignee of the present invention, and incorporated by reference. Briefly, considering the ingot meniscus, in this technique at least one perspective-view image of the ingot is acquired, and a feature detection process, such as an edge detection process, is then carried out on the image to locate the elliptical projection of the circular ingot meniscus into the image, and to compare the detected ingot contour with a hypothetical contour. The hypothetical contour is based on an expectation for the radius of the meniscus.

If the detected meniscus contour is found to correspond to the hypothetical contour, then numerical methods are employed to estimate the true contour and radius of the meniscus. If the detected meniscus contour is found not to correspond to the hypothetical contour, then the hypothesis is iteratively adjusted until correspondence is made. Appendix A presents an example of this procedure for fitting the equation of an ellipse to a set of detected edge points. Once the major and minor radii, a and b, respectively, of the ellipse are computed, the corresponding circular radius of the meniscus, in the physical coordinate system, can be ascertained using the transformation operations given previously. The ingot and crucible meniscus radii can be computed prior to the start of the ice detection process, or can be computed on-the-fly as the image sequence is produced.

Figures 12A, 12B:
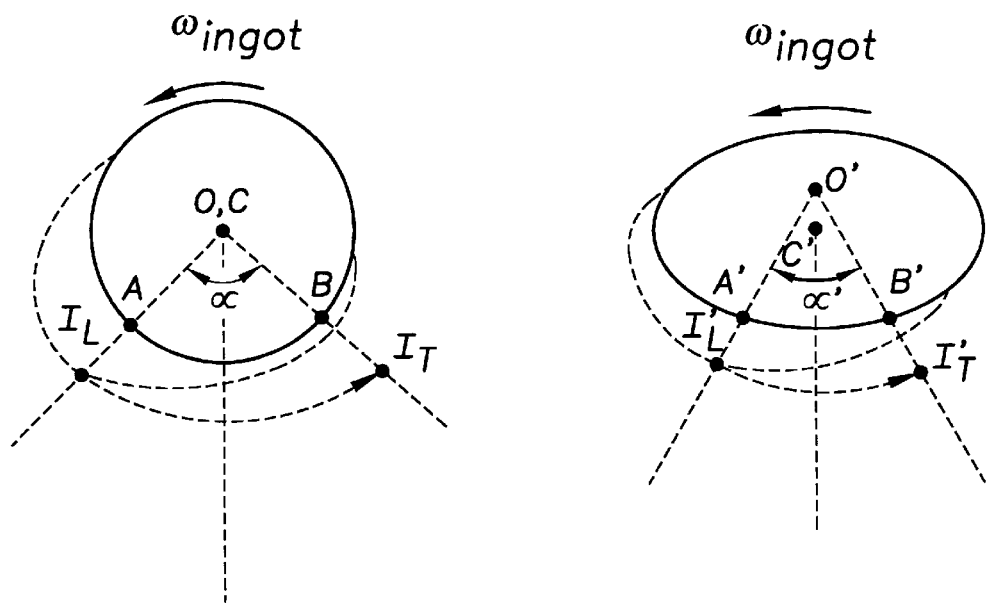
FIG. 12A is a schematic representation of a circular crystal ingot meniscus contour and ingot ice contour and the corresponding lead and trailing ice contour feature detector orientations, all corresponding to the physical coordinate system of the crystal ingot.
FIG. 12B is a schematic representation of a perspective-view elliptical projection of the contours and feature detector orientations of FIG. 12A, corresponding to the viewing coordinate system of an image acquisition camera.

Considering the configuration process for the ingot ice feature detectors, and referring to FIG. 12A, there is shown a geometric diagram of an orthogonal view of the physical coordinate system. The circle represents the ingot meniscus, having a center point, C, that coincides with the center of rotation, designated as the origin, O, of the coordinate system. The point A is a point on the ingot meniscus and on a selected radial line to which the lead feature detector is to be aligned. The point $I_L$ is an example ice point detected on the outer contour of a region of ingot ice that also lies on the selected radial line. Given the direction of ingot rotation shown in the figure, during one image acquisition period the detected ingot ice contour point $I_L$ rotates from the radial line common with point A through an arc of angle α to a second radial line common with the point B shown in the figure. The detected rotated ingot ice contour point here is designated as point $I_T$. The line common to points B and $I_T$ is a selected radial line to which the trailing feature detector is to be aligned.

To define the physical coordinates for the preferable locations of the lead and trailing radial lines, the rotation angle, α, is first determined as:

$$\alpha = \omega_{ingot} \cdot T_a; \tag{17}$$

where $\omega_{ingot}$ is the rotation rate of the ingot and $T_a$ is the image acquisition period. The rotation angle thus defines the arc through which a given feature point travels during one image acquisition period. In the example given in FIG. 12A the radial alignment lines for the lead and trailing feature detectors are separated by an arc corresponding to one image acquisition period, as given in relation (17), but it is to be understood that any practical integer multiple of acquisition periods can be considered for aligning the radial lines. The integer multiple can be a fixed constant or can be a variable value that is adjusted if and when changes in the ingot rotation rate are sensed.

Given the selected arc length between the lead and trailing radial alignment lines, a symmetry line is selected on which the arc is centered. As shown in FIG. 12A, in one example, a vertical symmetry line is selected such that the two radial lines are oriented toward the corners of an image field of view, whereby the longest possible feature detector rectangles can be provided. At this point, given the coordinates of the selected symmetry line, and given the numerical ingot meniscus radius as described above, the physical X-axis and Y-axis coordinates of the points A and B on the selected radial lines can be determined. For example, given the configuration of FIG. 12A, then for each of the points it can be determined:

$$X - \text{coordinate} = r\sin\frac{\alpha}{2}; \; Y - \text{coordinate} = r\cos\frac{\alpha}{2}. \quad (18)$$

The appropriate sign must also be associated with the coordinates for each point.

The origin point, O, (0, 0) and the coordinates for point A thereby specify the radial line along which the lead feature detector is to be aligned, in the physical plane, and the origin point and the coordinates for point B specify the radial line along which the trailing feature detector is to be aligned, again in the physical plane.

Recognizing that the feature detectors are in practice configured in perspective-view images rather than in an orthogonal view of the physical coordinate system, the coordinates for the ingot origin, O, and the points A and B are transformed, based on the expressions given previously, to the image coordinate system. The geometric result of this transformation is illustrated in the diagram of FIG. 12B. Here a projection of the circular ingot meniscus into the perspective-view image is an elliptical contour, as shown, where the center of the ellipse, at point C' is shifted from the center of rotation, O', which is shifted from the origin. Thus the ingot meniscus circle is here stretched to an ellipse and the center point of the meniscus circle in the physical coordinate system is transformed to a point in the image coordinate system that is shifted away from the ellipse center.

Transformation of the image coordinates for the ingot origin, 0, and the points A and B, to the elliptical image coordinate system is based on the camera calibration geometry as well as the known Z-axis melt location provided, as described above, in step 159. With this data, the relations (6)–(8) given above can be employed to make the coordinate transformation. This results in the specification of the coordinates for the locations of lead and trailing feature detectors for the ingot ice detection process.

Referring also to FIG. 10, this process for defining the feature detector locations is carried out in step 160 for the ingot and in step 162 for the crucible. In configuring the crucible ice feature detectors, and referring again to FIG. 11, it is to be recognized that if the detection process is directed to both ingot and crucible ice detection, then both the ingot feature detectors and the crucible feature detectors must be configured to operate within the same image field of view. In one scenario, a single lead feature detector and a single trailing feature detector are employed for detecting both ingot ice and crucible ice. In the example process of FIGS. 9–10, separate feature detector pairs are employed.

In this example scenario, the arc specified between lead and trailing crucible feature detectors 184, 186, respectively, does not need to coincide with that between the lead and trailing ingot feature detectors 180, 182. A geometric analysis like that provided above with respect to FIGS. 12A and 12B is carried out for the crucible feature detectors to define the radial line along which the detectors are specified in the perspective-view sequence of acquired images.

Given that each feature detector is a rectangular region aligned with a ray emanating from an elliptical center point of the acquired images, it is preferred that the detection regions be relatively narrow and of sufficient length to capture the melt surface, as shown in FIG. 11 and described above. An example detector width is about 5 pixels wide. In one example implementation of the feature detectors, each functions as an edge detection region that is configured to impose an edge search direction aligned with the ray along which that region is imposed. The ingot ice detectors preferably follow a search direction that is radially outward, while the crucible ice detector preferably follow a search direction that is radially inward, in each case such that the expected location of an ice region contour is closest to the starting end of the search path.

As is conventional, for each edge detection region the gradient of the image intensity profile is computed along the specified search direction, and then the peak in the resulting gradient profile that satisfies specified edge characteristics, such as minimum image intensity transition, is determined. If the found peak in any given edge detection region exceeds a configurable threshold, then it is judged that an edge has been detected in that region and the position of the edge in the image is recorded. Preferably, the edge detection tool seeks the strongest edge point along the full extent of each edge detection region. A confidence factor in the edge detection functionality can be imposed by requiring, e.g., that an edge be detected only for some intensity transition difference. It is to be recognized that other feature detectors and feature detector configurations can be employed.

Referring back to FIG. 10, once the feature detectors are configured, an iterative loop 166 is carried out a number, j=1 to M times, corresponding to the number, M, of object images specified for acquisition. In a first step 168 of the loop 166 an image of the crystal growth process is acquired. Then in a detection step 170a relating to the ingot ice and step 170b relating to the crucible ice, in each of the configured feature detectors there is detected the ice contour point which is nearest to the corresponding meniscus. For example, for the ingot ice feature detectors, the negative image intensity transition found to be nearest to the ingot meniscus radius is identified, given a radially-outward search direction, while the negative image intensity transition found to be nearest to the crucible meniscus radius is identified, given a radially-inward search direction.

In operation, each feature detector determines the one ice point found along the length of the detection region that meets this nearest edge criteria, and stores the corresponding meniscus point and ice contour point, referenced to the image coordinate system. Four tables, one for each feature detector, with entries for each of the Macquired images, are thus produced as the image acquisition loop progresses. Then in a next step 172a, 172b, the stored coordinates for the detected ice contour and meniscus points for a given image are transformed to an orthogonal, top-down and cross-sectional view, like that of FIG. 8A, using the specified Z-axis position of the melt surface in the transformation operation. Relations (9) and (10) above are here employed to carry out the transformation.

In the next step 174*a*, the distance from the ingot ice contour point identified by each ingot ice detector, and now referenced to the physical coordinate system, to the ingot meniscus, is determined and separately stored. Similarly, in step 174*b*, the distance from the crucible ice contour point identified by each crucible ice detector, now referenced to the physical coordinate system, to the crucible meniscus, is determined and separately stored. As can be recognized, the coordinate system transformation steps 172*a*, 172*b* above can include an embedded subtraction operation to determine the meniscus-ice distances as a function of the transformation, or the subtraction operation can be distinctly carried out before or after the transformation.

With this subtraction complete, a lead ingot ice width contour point, trailing ice width contour point, lead crucible ice width contour point, and trailing crucible ice width contour point are produced for the given $j^{th}$ image just acquired in the sequence of M images. In a next step 176 it is determined if a complete sequence of Mimages has been acquired and analyzed. A conventional counter and comparison technique can be employed to make this determination. If the number, M, of images has been acquired and analyzed, then the process moves to an end step 178. If less than the number, M, of images has been acquired and analyzed, then the loop 166 is continued to acquire and analyze the next $j^{th}$ image in the sequence.

Referring to FIG. 13A and FIG. 13B, once all Mimages have been acquired and analyzed, an ice width contour point value is produced for each image in the sequence for both the lead feature detector and the trailing feature detector. FIGS. 13A and 13B are example plots of such ice width point values for a lead and trailing feature detector, respectively, for, e.g., the ingot ice detection process. The plots correspond to the stored table of ice width values produced at step 174*a* and form an ice contour profile that encompasses at least one revolution of the crystal ingot.

The ice contour profile for the lead feature detector directly corresponds with the images in the sequence of acquired images. But the ice contour profile for the trailing feature detector does not make the same correspondence. Referring back to FIG. 12A, this is found to be due to the fact that a feature point detected at a given time, i.e., in a given image, by the lead feature detector, will be detected at a later time, i.e., in a later image in the sequence, by the trailing feature detector. If the lead and trailing feature detectors are configured such that a feature point will move from the lead feature detector to the trailing feature detector between consecutive images in the sequence, then the ice contour profile for the trailing detector will be offset by one image from that of the lead detector. Similarly, if some integer multiple of images separates the two images in which a feature appears first in the lead and then in the trailing feature detectors, then the ice contour profile for the trailing feature detector will be offset by that integer multiple.

It is thus preferred that once the sequence of images is acquired, or alternatively, as the steps are carried out to acquire and analyze the sequence, the ice contour profiles corresponding to the ingot and the crucible trailing feature detectors be remapped to directly correspond to the image sequence numbers for the ingot and crucible lead feature detectors. With this remapping, then as shown in FIGS. 13A–13B a direct correspondence between the lead and trailing ice contour profiles can be made. This is enabled by the fact that a feature point detected by a lead feature detector is the same distance from the origin of the coordinate system when that point has rotated to be detected by the trailing feature detector.

Referring back to FIG. 9, in the process for detecting the ingot and meniscus ice in the crystal growth process, in a next step 136*a*–136*d*, the ice width contour image data produced for the sequence of M images, as shown, e.g., in FIGS. 13A–13B, is processed in a blurring operation. By "blurring operation" is here meant a machine vision process in which a selected structural element size, i.e., pixel group, is applied to the contour pattern. In one example blurring operation, each feature of a 1×1 pixel size in the contour patterns is expanded, using a 3×3 structural element, so that each 1×1 pixel feature becomes a 3×3 pixel feature. In other words, each feature of a single pixel in width and height is expanded in all directions to become a 3×3 feature. A machine vision dilation tool can be applied in a conventional manner to produce the blurring operation.

The blurring operation compensates for inaccuracies in the detection process that are due to fluctuations in the imaged scene. The crystal growth process environment is an inherently noisy environment in which stray optical and electrical data can be inadvertently incorporated into an analysis process, and which can unpredictably change due to crystal ingot geometry, melt surface and/or crucible reflectance characteristics, and other such conditions. The blurring step accounts for the imprecision in ice contour detection that results from this noise and variability of the growth environment. Thus, as can be recognized, the blurring operation can be tailored to the expected conditions of the process under analysis. Historical data relating to the system accuracy, stability, and other related characteristics can be analyzed to determine appropriate blurring parameters; whereby higher variance in the data directs an increase in the blurring parameters.

In the next step 138*a*, 138*b*, the blurred lead ingot ice contour is logically ANDed with the blurred trailing ingot ice contour, and the blurred lead crucible ice contour is logically ANDed with the blurred trailing crucible ice contour, respectively. A validated ingot ice contour and a validated crucible ice contour are produced as a result of the ANDing operations. Specifically, a pixel-by-pixel logical AND of each corresponding lead and trailing ice width contour image, like that of FIGS. 13A–13B, is carried out, and a valid ice contour is constructed corresponding to the AND result. In other words, where a contour point value is found to coincide in the images, e.g., at image numbers 1, 2, and 4 in the two plots, a validated contour point of the corresponding value will be constructed for image numbers 1, 2, and 3 in the validated contour image; in contrast, where a contour point value is not found to coincide in the two images, e.g., at image numbers 3, 7, and 10, no contour point will be included in the validated contour image.

The ANDing operation, in conjunction with the blurring operation, increases the robust nature of the detection process even under the noisy and unpredictable conditions of the crystal ingot growth environment. The resulting validated ice contours can be represented by a sequence of contour images, like that of FIGS. 13A–13B, but possibly including more than one contour point value for each image in the sequence, as a result of the blurring operation. Further, residual noise data may have sustained the ANDing operation to remain in the contour data. In addition, along with any original gaps in the contour data, the ANDing operation may have produced additional gaps in the data.

Ideally, the validated ice contours include only one contour point value for each image, with all redundant points, i.e., extra points inserted due to the blurring operation, discarded, and missing point values interpolated based on the existing data. Each contour point then corresponds to a unique image in the sequence, and each image in the sequence provides one single contour point value. With this final arrangement, a meaningful interpretation of the contour data can be made.

In one technique for producing this desired final contour, in a next step 140a, 140b of the process, filtering and interpolation operations are applied to the validated contours. In one example, preferable technique, an interpolation process is carried out as an energy minimization operation that employs an energy function to describe the state of the final image system, where the system represents a 1-dimensional data set that is the single contour point image sequence.

In one implementation of this operation, utilizing an active contour model, often called a "snake," the ice contour is represented as an elastic curve having a set of control points, one point corresponding to each of the images in the sequence. The initial snake control point values are set to zero, and then iteratively adjusted to deform the elastic curve from its initial shape to a final shape for which the energy level is minimized. The energy function for the snake is given as:

$$E_{snake} = \sum_{i=1}^{M} (E_{int}(i) + E_{ext}(i)); \quad (19)$$

where M is the size of the snake, equal to the number of acquired images in the image sequence for the validated ice contour; and where the internal energy function, $E_{int}$, defined to constrain the tension and bending of the snake curve, is given as:

$$E_{int}(i) = a\|r_i - r_{i-1}\|^2 + b\|r_{i-1} - 2r_i + r_{i+1}\|^2; \quad (20)$$

where $r_i = (x_i, y_i)$ is the contour value coordinate of the $j^{th}$ image snake point, a is a constant imposing the tension constraint between two adjacent snake points, and b is a constant imposing the bending constraint among three neighboring snake points; and where the external energy function, $E_{ext}$, defined to impose feature matching correspondences, is given as a negated gaussian function of:

$$E_{ext}(i) = -\sum_{n=0}^{P-1} e^{-\frac{(r_i - r_n)^2}{2\sigma^2}}; \quad (21)$$

where in this negated gaussian function P is the number of contour data points in each image of the validated contour image, and σ is the characteristic of the gaussian function. These energy functions and their implementation as an active contour model are described further in "A Neural Network-Based Stochastic Active Contour Finding of Distinct Features," *IEEE Trans. on Image Proc.*, V. 4, N. 10, pp. 1407–1416, October, 1995.

With these energy functions implemented for a given validated ice contour, then an iterative energy minimization method is applied to determine an optimum set of snake control point values that minimizes the energy level of a 1-dimensional system. As explained above, the resulting 1-dimensional system defines a single contour profile point value for each image in the sequence, thereby eliminating any remaining noise by replacing the initial, perhaps redundant, contour point values of each image with a single contour point value.

One example and preferred minimization method is the conventional Fletcher-Reeves-Polak-Ribiere minimization method, described in *Numerical Recipes in C*, by Press, Flannery, Teukolsky, and Vettering, Cambridge University Press, pp. 317–324, 1988. In one example implementation, the values for the constants can be set as a=0.00005, b=0.0005, and σ=25. This implementation is found to successfully interpolate across gaps in the data and to remove extraneous noise.

Once the validated ingot and crucible ice contours are filtered and analyzed for interpolation of the contour, if needed and desired, then in a next step 144a, 144b, the area of the ingot ice region and the area of the crucible ice region, respectively, can be estimated with a high degree of confidence. The area estimation computations can be carried out using any suitable, conventional technique. For example, a conventional numerical addition method, or other suitable method, can be employed to sum together the ice width contour values that have been stored for the finalized validated contour images. If desired, the computed ice width estimation values, or some index relating to the values, can be reported to the process operator via the user interface (74 in FIG. 6) of the image processing system.

In a following step 144a, 144b, the widest contour span point of the ingot ice region and the crucible ice region, respectively, is determined. This can be accomplished by a comparison operation in which the largest value in each validated contour is identified.

In a final step 146, the width of the ice-free annulus of melt surface existing between the widest point of the ingot-related ice and the widest point of the crucible-related ice is computed. This configuration corresponds to the instant, as the ingot and the crucible rotate in opposite directions, that the widest points of the two ice regions pass each other, and determines how close the two regions are to bridging together. Given that the widest contour span point of each of the two ice regions is a value of ice width, and given that the ingot meniscus radius and the crucible meniscus radius were each previously determined, a numerical subtraction operation can be carried out to determine the distance between the widest ingot ice point and the widest crucible ice point. The computed ice-free melt width can then be reported to the process operator to enable appropriate emergency procedures for safeguarding the growth apparatus from damage and for salvaging as much of the ingot as is possible.

As can be recognized, this ice detection process can be adapted to accommodate a wide range of scenarios. For example, the process can be employed to detect ingot ice alone, to detect crucible ice alone, or to detect the presence of the two ice regions without computing the distance between the regions. As explained above, any reasonable number of feature detection points can be configured for analyzing images of the acquired image sequence; with multiple, distinct validation operations carried out for distinct features.

As can be further recognized, the capabilities of this example ice detection process can be adapted and extended to other machine vision applications. The process provides the ability to produce a circumferential feature profile on a complicated three-dimensional object and to analyze aspects of the features along the profile. This can be generalized to a method for ascertaining an orthogonal view of some object plane, even a cross-sectional circumferential plane, of a three-dimensional object, and even when regions of the object obscure other object portions required for reconstruction of the desired orthogonal view. In the semiconductor crystal growth process, the growing ingot obscures portions of the ingot, the melt, the ingot meniscus, the crucible meniscus, and ingot and crucible ice regions in a perspective-view image of the growth process. But the machine vision process of the invention overcomes this limitation to produce a representation of the entire ingot, melt, and crucible regions. The technique thereby enables the extraction of various two-dimensional feature information from a complicated three-dimensional configuration. It is of particular note that this can be accomplished in accordance with the invention with the use of only one camera, where a human interpretation of the three-dimensional configuration requires stereo optical processing of the image. It is to be recognized, however, that for a suitable application, more than one camera can be employed. A multi-camera configuration enables simultaneous analysis of multiple feature planes of interest, enables analysis of opposing sides of a feature surface, and enables three-dimensional analysis of object feature orientations.

The process further provides the ability to validate detected profile features to thereby enhance the integrity of any following feature analysis. In the semiconductor crystal ingot growth process, stray optical reflectance, electrical signal noise, unpredictable variability in the surface characteristics of the growing ingot, the melt, and the crucible, and other such factors limit the credibility of the results of the ice feature detection processes. The machine vision process of the invention provides feature detection results of high integrity by compensating for this condition with a coincidence analysis in which stray, extraneous noise data is rendered transparent to the feature analysis. The technique thereby enables feature detection and analysis even in noisy and unpredictable detection environments.

The machine vision techniques of the invention can thus be applied to a wide range of applications where feature analysis of a complicated three-dimensional configuration is required. The profile of an object at some position along an axis of the object can be determined for, e.g., inspection purposes. Glass blowing, cable twisting, and molding operations can here be monitored in real time to ensure correct part production. Where the profile position of interest does not include distinctive lighting or surface relief features, a line of light can be projected at the position of interest to enable detection of points along that position. In other applications, several object profiles taken at different positions along an object can be analyzed to enable various determinations about the object. In other applications, the presence of a required surface feature along a line or lines on an object can be confirmed, or the configuration of an object with respect to a tooling or processing set up can be confirmed.

It is thus to be recognized that the invention contemplates wide applicability of the machine vision techniques described above. Complicated and unpredictable three-dimensional object and feature sizes and shapes are accommodated by the techniques as surface feature information is extracted and analyzed. Extraneous and faulty feature data is rendered transparent to feature analysis processes to enhance the integrity of the processes. Only one camera is required to produce a complete representation of an object even for applications where some object regions may obscure others. A wide range of feature analysis techniques, including a technique for analyzing the spacing and symmetry of features along a cross-section circumferential profile, are enabled. It is recognized, of course, that those skilled in the art may make various modifications and additions to the image acquisition and feature analysis techniques described above without departing from the spirit and scope of the present contribution to the art. Accordingly, it is to be understood that the protection sought to be afforded hereby should be deemed to extend to the subject matter of the claims and all equivalents thereof fairly within the scope of the invention.

Appendix A

In an example process for fitting the parameters of an ellipse to a set of detected ellipse points, first is solved a system of four linear equations whose coefficients are computed from the set of detected points. The solution to the linear system is then imposed on a set of nonlinear equations to derive the ellipse parameters of the center point $(x_c, y_c)$, the major axis, a, and the minor axis, b.

The equation of an ellipse is given as:

$$\frac{(x-x_c)^2}{a^2} + \frac{(y-y_c)^2}{b^2} = 0; \tag{a}$$

or equivalently:

$$x^2 + c_1 \cdot x + c_2 \cdot y^2 + c_3 \cdot y + c_4 = 0, \tag{b}$$

where:

$c_1 = -2 \cdot x_c$, $c_2 = a^2/b^2$, $c_3 = -2 \cdot (a_2/b_2) \cdot y_c$, and $c_4 = x_c^2 + (a^2/b^2) \cdot y_c^2 - a^2$.

Given a number, n, of detected ellipse coordinate points, $(x_i, y_i)$, where i=1 to n, a mean squared error, E, is given as:

$$E = \sum_{i=1}^{n} (x_i^2 + c_1 \cdot x_i + c_2 \cdot y_i^2 + c_3 \cdot y_i + c_4)^2. \tag{c}$$

The minimum of the error value, E, can be obtained by solving for the four constants, $c_1$, $c_2$, $c_3$, and $c_4$, that satisfy the normal equations:

$$0 = \frac{\partial E}{\partial c_1} = 2\sum_i [x_i \cdot (x_i^2 + c_1 \cdot x_i + c_2 \cdot y_i^2 + c_3 \cdot y_i + c_4)] \tag{d}$$

$$0 = \frac{\partial E}{\partial c_2} = 2\sum_i [y_i^2 \cdot (x_i^2 + c_1 \cdot x_i + c_2 \cdot y_i^2 + c_3 \cdot y_i + c_4)] \tag{e}$$

$$0 = \frac{\partial E}{\partial c_3} = 2\sum_i [y_i \cdot (x_i^2 + c_1 \cdot x_i + c_2 \cdot y_i^2 + c_3 \cdot y_i + c_4)] \tag{f}$$

$$0 = \frac{\partial E}{\partial c_4} = 2\sum_i [x_i^2 \cdot (x_i^2 + c_1 \cdot x_i + c_2 \cdot y_i^2 + c_3 \cdot y_i + c_4)] \tag{g}$$

where $$\frac{\partial E}{\partial c_1}$$

denotes the partial differentiation of E with respect to $c_1$.

The above expressions (d)–(g) with four unknowns can be written in matrix form as:

$$\begin{bmatrix} \sum_i x_i^2 & \sum_i x_i \cdot y_i^2 & \sum_i x_i \cdot y_i & \sum_i x_i \\ \sum_i x_i \cdot y_i^2 & \sum_i y_i^4 & \sum_i y_i^3 & \sum_i y_i^2 \\ \sum_i x_i \cdot y_i & \sum_i y_i^3 & \sum_i y_i^2 & \sum_i y_i \\ \sum_i x_i & \sum_i y_i^2 & \sum_i y_i & n \end{bmatrix} \begin{bmatrix} c_1 \\ c_2 \\ c_3 \\ c_4 \end{bmatrix} = \begin{bmatrix} -\sum_i x_i^3 \\ -\sum_i x_i^2 \cdot y_i^2 \\ -\sum_i x_i^2 \cdot y_i \\ -\sum_i x_i^2 \end{bmatrix} \quad (h)$$

After solving the above matrix expression for the constants, $c_1$, $c_2$, $c_3$, and $c_4$, the constants are imposed on the expressions (a) and (b) above to produce the resulting center point coordinates of the ellipse as:

$$x_c = -c_1/2 \text{ and } y_c = -c_3/(2 \cdot c_2). \quad (i)$$

The major and minor radii, a, and b, respectively, of the ellipse are then given as:

$$a = \sqrt{-c_4 + \frac{c_1^2}{4} + \frac{c_3^2}{4c_2}} \text{ and } b = \sqrt{\frac{1}{c_2}\left(-c_4 + \frac{c_1^2}{4} + \frac{c_3^2}{4c_2}\right)} \quad (j)$$

These expressions for the ellipse center point, ellipse major axis, and ellipse minor axis are evaluated for the image coordinate system projection of the circular ingot meniscus and circular crucible meniscus, as described above, and then transformed to the physical coordinate system to ascertain the physical radius of the circular ingot meniscus and the circular crucible meniscus.

The physical Z-axis location of the melt surface can then be determined as:

$$z = \frac{f + d}{(a^2 + f^2) \cdot \sin(\theta) + f \cdot y_c \cdot \cos(\theta)} \cdot \quad (k)$$

$$[f \cdot y_c + a^2 \cdot \sin(\theta) \cdot \cos(\theta)];$$

where $f$ is the focal length of the image acquisition camera, and $\theta$ is the viewing angle, both as defined in FIG. 2. The resulting z value is the location along the physical Z-axis of the melt surface.

We claim:

1. A machine vision method for detecting features of an object in a selected feature plane of the object, the method comprising:

acquiring a sequence of images of the object from a fixed viewing location as the object rotates about a selected object axis, each image in the sequence corresponding to a distinct orientation of the object about the selected object axis, the sequence of acquired object images comprising at least a minimum number, M, of object images, where M is selected as $M = T_0/T_a$, where $T_0$ is a period of revolution of the object and $T_a$ is a period required for acquiring one image;

inspecting images in the image sequence for feature points of the selected feature plane, as projected into the images, at a number, n, of feature detection locations, the feature detection locations configured with respect to each other at image positions based on an expected shift in image location of a given feature point between two consecutive images in the image sequence;

associating detected feature points with an orthogonal-view representation of the selected feature plane; and identifying as valid object feature points those feature points detected in a specified minimum number of the n feature detection locations each in a different image of the image sequence.

2. A machine vision method for detecting features of an object in a selected feature plane of the object, the method comprising:

acquiring a sequence of images of the object, each image in the sequence corresponding to a distinct orientation of the object about a selected object axis;

inspecting images in the image sequence for feature points of the selected feature plane, as projected into the images, at a number, n, of feature detection locations, by:
applying an edge detection region at each of the n feature detection locations,
searching each edge detection region for an edge of an object feature point; and
correlating positions of detected edges to object feature point positions, the feature detection locations configured with respect to each other at image positions based on an expected shift in image location of a given feature point between two consecutive images in the image sequence;

associating detected feature points with an orthogonal-view representation of the selected feature plane; and identifying as valid object feature points those feature points detected in a specified minimum number of the n feature detection locations each in a different image of the image sequence.

3. A machine vision method for detecting features of a semiconductor melt surface from which a semiconductor crystal ingot is pulled as the ingot and melt are rotated about a vertical axis of rotation, the method comprising:

acquiring a sequence of perspective-view images of the melt surface from a fixed viewing location, each image in the sequence corresponding to a perspective view of a distinct orientation of the melt about the vertical axis of rotation;

inspecting images in the image sequence for melt surface feature points, as projected into the images, at a number, n, of feature detection locations, the feature detection locations configured with respect to each other at image positions based on an expected shift in image location of a given melt surface feature point between two consecutive images in the image sequence;

mapping detected melt surface feature points from a perspective-view image projection to an orthogonal-view projection of the melt surface; and identifying as valid melt surface feature points, comprising contour points of solid-phase crystal regions on the surface of the melt, those feature points detected in a specified minimum number of the n feature detection locations each in a different image of the image sequence.

4. The method of claim 3 further comprising analyzing the solid-phase crystal region contour points to determine solid-phase crystal region area.

5. The method of claim 3 further comprising analyzing the solid-phase crystal region contour points to determine an extent of the melt surface that is free of the solid-phase crystal.

6. The method of claim 4 wherein inspecting images for melt surface feature points comprises inspecting images for a solid-phase crystal region nucleating at the ingot.

7. The method of claim 4 wherein inspecting images for melt surface feature points comprises inspecting images for a solid-phase crystal region nucleating at a wall of a crucible in which the melt is contained.

8. The method of claim 7 wherein inspecting images for melt surface feature points further comprises inspecting images for a solid-phase crystal region nucleating at the ingot.

9. The method of claim 8 further comprising analyzing the solid-phase crystal region contour points to determine an extent of the melt surface between solid-phase crystal regions nucleating at the ingot and nucleating at the crucible that is free of solid-phase crystal.

* * * * *